United States Patent
Vyas et al.

(10) Patent No.: US 12,247,180 B2
(45) Date of Patent: Mar. 11, 2025

(54) APPARATUS AND COMPOSITIONS FOR IMPROVING SCENT DELIVERY

(71) Applicant: The Procter & Gamble Company, Cincinnati, OH (US)

(72) Inventors: Rahul Vyas, Singapore (SG); Desmond Ng, Singapore (SG); Garima Chauhan, Singapore (SG); Gaurav Saini, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 790 days.

(21) Appl. No.: 17/354,092

(22) Filed: Jun. 22, 2021

(65) Prior Publication Data

US 2022/0002633 A1    Jan. 6, 2022

Related U.S. Application Data

(60) Provisional application No. 63/047,271, filed on Jul. 2, 2020.

(51) Int. Cl.
| | | |
|---|---|---|
| *C11B 9/00* | (2006.01) | |
| *A61L 9/04* | (2006.01) | |
| *A61L 9/12* | (2006.01) | |

(52) U.S. Cl.
CPC ............ *C11B 9/0015* (2013.01); *A61L 9/042* (2013.01); *A61L 9/048* (2013.01); *A61L 9/127* (2013.01); *C11B 9/0023* (2013.01); *C11B 9/0034* (2013.01); *C11B 9/0061* (2013.01)

(58) Field of Classification Search
CPC .......... A61L 9/014; A61L 9/042; A61L 9/048; A61L 9/127; A61L 9/01; C11B 9/0034; C11B 9/0023; C11B 9/0061; C11B 9/0015
USPC ....................................................... 512/2, 1
See application file for complete search history.

(56) References Cited

U.S. PATENT DOCUMENTS

| | | | |
|---|---|---|---|
| 8,338,346 B2 * | 12/2012 | Diersing ................... | A61L 9/01 512/26 |
| 8,603,963 B1 | 12/2013 | Steward | |
| 8,882,998 B2 | 11/2014 | Tranzeat et al. | |
| 9,642,927 B2 | 5/2017 | Hollingshead et al. | |
| 9,827,342 B2 | 11/2017 | Morgan et al. | |
| 10,322,198 B2 | 6/2019 | Morgan, III et al. | |
| 10,336,966 B2 | 7/2019 | Holland et al. | |
| 10,407,644 B2 | 9/2019 | Blondeau et al. | |
| 2009/0257973 A1 | 10/2009 | Fraser et al. | |
| 2013/0336914 A1 | 12/2013 | Horenziak et al. | |
| 2018/0008740 A1 | 1/2018 | Morgan, III et al. | |
| 2018/0180391 A1 * | 6/2018 | Holland ................. | A61K 8/492 |
| 2022/0002632 A1 * | 1/2022 | Vyas ..................... | C11B 9/0015 |

FOREIGN PATENT DOCUMENTS

| | | |
|---|---|---|
| JP | 2001104462 A | 4/2001 |
| WO | 2018091686 A1 | 5/2018 |
| WO | 2020028340 A1 | 2/2020 |

OTHER PUBLICATIONS

All Office Actions; U.S. Appl. No. 17/354,081, filed Jun. 22, 2021.
U.S. Appl. No. 17/354,081, filed Jun. 22, 2021, to Rahul Vyas et. al.
PCT Search Report and Written Opinion for PCT/US2021/039752 dated Oct. 26, 2021, 19 pages.

* cited by examiner

*Primary Examiner* — Jessica Whiteley

(74) *Attorney, Agent, or Firm* — Elizabeth A. Conklin; Carolyn S. Powell; Abbey A. Lopez

(57) ABSTRACT

A volatile composition having: (i) greater than 30% of a scented hydrophobic material by weight of the volatile composition, wherein the scented hydrophobic material comprises one or more volatile compounds; and (ii) greater than 20% of a regulating scent intensity (RIS) composition by weight of the volatile composition.

The RIS composition has at least two of:

a first regulating scent intensity component (RIS component) having a high average vapor pressure (VP);

a second RIS component having a medium average VP; and a third RIS component having a low average VP;

The average VP of each of said one or more volatile compounds is lower than at least one of the high, medium and low average VPs of the first, second and third RIS components at the same temperature.

20 Claims, 11 Drawing Sheets

APPARATUS AND COMPOSITIONS FOR IMPROVING SCENT DELIVERY

FIELD OF THE INVENTION

The present invention relates to an apparatus and a volatile composition comprising a scent intensity regulating composition for improving scent delivery in an interior space.

BACKGROUND OF THE INVENTION

Devices for dispensing volatile materials are well known and commonly used to deliver a variety of benefits such as freshening, malodor removal or scenting of air in spaces in household and commercial establishments such as rooms, or enclosed spaces such as a toilet, a vehicle passenger compartment space.

For example, air freshening products have been designed for dispensing volatile materials such as a volatile composition comprising one or more volatile materials, such as perfume oils. The volatile composition may be contained and dispensed through systems such as via evaporating the volatile composition from membrane based, wick based and gel based systems. However, a problem with such air freshening products is often an inconsistency in the evaporation rate of the volatile composition over the product life, i.e. high evaporation rate of the volatile composition at the beginning of product use and low evaporation rate towards end of product life.

Specifically, the volatile composition typically comprises a mixture of highly volatile compounds and other volatile compounds which are less volatile ("less volatile compounds"). Highly volatile compounds generally have higher vapor pressures than the less volatile compounds. Specifically, at a given temperature, a highly volatile compound with a higher vapor pressure vaporizes more readily than a less volatile compound with a lower vapor pressure. In use, the highly volatile compounds tend to evaporate more quickly at the beginning of such a product's use, while the less volatile compounds evaporate later, resulting in an overall inconsistent scent intensity and fragrance character of the volatile composition over the product life. The high initial evaporation rate can result in an overpowering initial scent intensity which can create a perception that the air freshener product has a different scent intensity over the product life or that the product is no longer effective after the initial scent intensity is no longer present.

Further, the problem of inconsistency in the evaporation rate is exacerbated at a user's first interaction with air in an interior space (hereinafter "First Touch Point"). The interior space may in a vehicle, a residential building, a commercial building, or any part or room in the residential/commercial building.

Typically, the air at the First Touch Point is a mixture of pre-existing or predominant odors in the interior space. This can create an unpleasant First Touch Point to the user upon entry, i.e. at the entrance of the interior space. Further, especially when visitors enter the interior space, having an unpleasant First Touch Point also creates an unfavorable impression for subsequent engagement and activities in the interior space.

In some cases, carriers such as solvents and diluents are used to slow down the rate of evaporation of a volatile composition such as for example a volatile freshening composition. In highly volatile freshening compositions, a high level of carriers may be used to slow down the evaporation of the freshening composition. Adding carriers and other materials to slow down the evaporation rate of the freshening composition may significantly reduce the level of perfume raw materials in the freshening composition or may change the character of the freshening composition and scent intensity.

Thus, it would be beneficial to provide a scent intensity regulating composition that can be used in a volatile composition to improve scent delivery of the volatile composition at the First Touch Point and/or provides a long-lasting scent irrespective of the vapor pressure of the volatile composition without significantly altering the formulation or character of the volatile composition.

SUMMARY OF THE INVENTION

The present invention relates to a volatile composition comprising:
  (i) greater than 30% of a scented hydrophobic material by weight of the volatile composition, wherein the scented hydrophobic material comprises one or more volatile compounds; and
  (ii) greater than 20% of a regulating scent intensity (RIS) composition by weight of the volatile composition, wherein the RIS composition comprises at least two of:
  a first regulating scent intensity component (RIS component) having a high average vapor pressure (VP);
  a second RIS component having a medium average VP; and
  a third RIS component having a low average VP;
  wherein the average VP of each of said one or more volatile compounds is lower than at least one of the high, medium and low average VPs of the first, second and third RIS components at the same temperature.

DETAILED DESCRIPTION OF THE INVENTION

Figure 1:
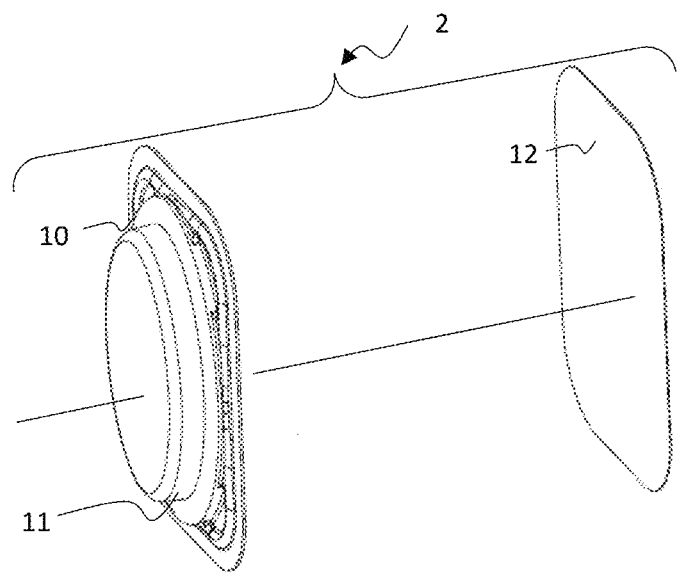
FIG. 1 is a perspective view of components of an apparatus for delivering a volatile composition according to the present invention.

The present invention relates to an apparatus and a volatile composition comprising a scent intensity regulating composition (hereinafter "RIS composition") for improving scent delivery in an interior space.

Perfume raw materials (hereinafter "PRMs") are typically used for providing scent in a volatile composition. Specifically, the volatile composition typically comprises a mixture of highly volatile PRMs and other volatile PRMs which are less volatile. Highly volatile PRMs generally have higher vapor pressures than the less volatile PRMs. Specifically, at a given temperature, a highly volatile PRM with a higher vapor pressure vaporizes more readily than a less volatile compound with a lower vapor pressure. However, because of the vapor pressures of the PRMs, the highly volatile PRMs tend to evaporate more quickly at the beginning of such a product's use, while the less volatile PRMs evaporate later, resulting in an overall inconsistent scent intensity and fragrance character of the volatile composition over the product life. The high initial evaporation rate can result in an overpowering initial scent intensity which can create a perception that the air freshener product has a different scent intensity over the product life or that the product is no longer effective after the initial scent intensity is no longer present.

The present invention is based on the surprising discovery that a volatile composition comprising greater than 30% of a scented hydrophobic material by weight of the volatile composition, wherein the scented hydrophobic material comprises one or more volatile compounds; and greater than 20% of a regulating scent intensity (RIS) composition by weight of the volatile composition, can deliver the one or more volatile compounds at a reduced initial evaporation rate and scent intensity over time without being impacted by temperature and/or air flow effects from the environment (i.e. the interior space which the volatile composition is placed). A volatile composition of the present invention having the combination of claimed levels of the scented hydrophobic material and the RIS composition does not significantly alter a scent character of the volatile composition while delivering a reduced scent intensity as demonstrated in results as described hereinafter under Examples) thereby producing improved scent delivery.

The RIS composition comprises at least two of: a first regulating scent intensity component (RIS component) having a high average vapor pressure (VP); a second RIS component having a medium average VP; and a third RIS component having a low average VP;

wherein the average VP of each of said one or more volatile compounds is lower than at least one of the high, medium and low average VPs of the first, second and third RIS components at the same temperature.

A RIS composition of the present invention may comprise, at least two of: a first scent intensity regulating component (RIS component) having an average vapor pressure (VP) greater than 0.3 Torr at 25° C.; a second RIS component having an average VP from 0.07 to 0.3 Torr at 25° C.; and a third RIS component having an average VP from 0.0099 to 0.07 Torr at 25° C., wherein each of the first, second, and third RIS components is characterized by an Odor Detection Threshold (ODT) of greater than 20 ppb, can be added to a volatile composition comprising PRMs to deliver the PRMs at a reduced initial evaporation rate and scent intensity over time without being impacted by temperature and/or air flow effects from the environment (i.e. the interior space which the volatile composition is placed).

A technical effect of the RIS composition having at least two of the first, second and third RIS components, each RIS component having different average vapor pressures at 25° C. instead of a single RIS component is that each of the at least two RIS components can act individually to slow down a respective evaporation rate of individual volatile compounds having different individual vapor pressures in a volatile composition. Specifically, the first RIS component can evaporate faster than a first volatile compound having a vapor pressure lower than 0.3 Torr at 25° C. thereby slowing an evaporation rate of the first volatile compound. Accordingly, the second RIS component can evaporate faster than a second volatile compound having a vapor pressure lower than 0.07 Torr at 25° C. and the third RIS component can evaporate faster than a third volatile compound having a vapor pressure lower than 0.0099 Torr at 25° C.

The volatile compounds may be designed to evaporate to provide a benefit in an interior space. One or more of the volatile compounds may be a benefit agent for delivering a benefit in the interior space. The benefit agent may include but is not limited to perfumes for providing a scent benefit, a malodor counteractant for removing malodor. A technical effect of slowing down the evaporation rate of the volatile compounds is to enable a controlled release of the benefit of the volatile component. Further, each of the RIS components is designed to be non-odorous by having an Odor Detection Threshold (ODT) of greater than 20 ppb.

For the purposes of illustrating the present invention in detail, the RIS composition described below is used for formulating a volatile composition with perfume raw materials (PRMs) for delivering a scent benefit in an interior space and accordingly the volatile composition is described as a perfume composition. The RIS composition may also be used for formulating a volatile composition with PRMs for freshening air in an interior space in a continuous non-energized manner and accordingly the volatile composition is described as an air freshening composition. However, it is contemplated that the RIS composition may be configured for use in a variety of applications to deliver a benefit in the interior space. Prior to describing the present invention in detail, the following terms are defined for clarity. Terms not defined should be given their ordinary meaning as understood by a skilled person in the relevant art.

"Odor Detection Threshold (ODT)" as used herein refers to a minimum concentration of a material that can be detected by a human nose and is determined according to an ODT method described in U.S. Pat. No. 9,827,342B2 issued in the name of The Procter & Gamble Company which published on Nov. 28, 2017 (hereinafter "U.S. Pat. No. 9,827,342"). Specifically, ODT of individual perfume raw materials (PRMs) or individual RIS components can be calculated using the test method outlined in U.S. Pat. No. 9,827,342, based directly on the molecular structure of the given PRM or the given RIS component, and expressed in units of ppb. ODT may be determined a software titled "winMolconn", release version—1. 0. 1. 3, commercially available and provided by software provider—Hall Associates Consulting, Quincy, Mass., U.S.A. at www.molconn.com.

"Molar Olfactive Index (MOI)" as used herein refers to an index that quantifies an odor intensity of a material into a value based on equations described hereinafter. A composition having a higher MOI value correlates to a higher odor intensity relative to another composition having a lower MOI value. Accordingly, a perfume composition having a higher MOI value corresponds to a higher scent intensity relative to another perfume composition having a lower MOI value.

"C log P" as used herein refers to a calculated log P ("C log P") value of a PRM. An octanol/water partition coefficient of a PRM is the ratio between its equilibrium concentrations in octanol and in water. The partition coefficients of the PRM used in a freshening composition may more conveniently be given in the form of its logarithm to the base 10, Log P. The C log P is determined by a model that computes the octanol-water partition coefficient (log P or log Kow) for general organic molecules based directly on molecular structure. Log P is a measure of the distribution of a solute between two immiscible liquid phases, octanol and water, and is generally used as a relative measure of the hydrophobicity of a solute. One way of computing Log P of a PRM is using the ACD/Labs Log P software module from Advanced Chemistry Development, Inc. Details of the calculation of log P can be found on the ACD/Labs website (https://www.acdlabs.com/products/percepta/predictors/logp/). Log P values of PRMs calculating using the ACD/Labs Log P software module and the Log P values of PRMs are used in the selection of PRMs which are useful in the present invention as described hereafter in the Examples. However, it will be appreciated that another suitable way of measuring Log P is using the "C log P" program from BioByte Corp (e.g., C log P Version 4.0 and Manual 1999). C LOG P USER GUIDE, Version 4.0, BioByte Corp (1999) (http://www.bio-byte.com/bb/prod/clogp40.html). A further suitable way of measuring Log P is using C LOG P program from Daylight Chemical Information Systems, Inc. of Alison Viejo, CA. The C LOG P Reference manual, Daylight Version 4.9, Release Date Jan. 2, 2008.

"Horizontal orientation" as used herein, refers to a position of an air freshening product according to the present invention wherein the membrane is facing the environment in an upward or downward position.

"Interior space" refers to a finite volume of space in an environment including but not limited to a residential, commercial or vehicle environment. The interior space may be a room in a residential or commercial environment such as for example a sanitary facility. The sanitary facility may include a bathroom, a toilet, a bathroom containing a toilet, a locker room. The interior space may also be an enclosed space such as for example, furniture for storage of personal items including but not limited to shoe cabinets, wardrobes, gym lockers.

"Membrane" as used herein, refers to a semi-permeable material which allows some components of matter to pass through but stops other components. Of the components that pass through, the membrane moderates the permeation of components i.e. some components permeate faster than other components. Such components may include molecules, ions or particles.

"Microporous membrane" as used herein, refers to a material having a network of pores.

"Natural convection" as used herein, refers to a type of flow, of motion of a liquid such as water or a gas such as air, in which the fluid motion is not generated by any external source (like a pump, fan, suction device, etc.) but by some parts of the fluid being heavier than other parts.

"Non-energized" means that the product is passive and does not require to be powered by a source of external energy. In particular, the product does not need to be powered by a source of heat, gas or electrical current. The product may also be configured as an energized device. An exemplary energized device may be an electrical device. The energized device may be an electrical car outlet or battery-operated air freshener having a wick and/or a membrane as described in the following description to transport a freshening composition and/or evaporate a freshening composition therefrom; or other heating devices (e.g. devices powered by chemical reactions such as catalyst fuel systems; solar powered devices, etc.).

"Permeable material" as used herein, refers to any material that allows liquids or gases to pass through, and includes, but is not limited to, drywall, wall paper, wood, vinyl, plastic, plaster, wallboard, fabrics, upholstery, paper, wovens, natural polymers, synthetic polymers and inorganic materials and mixtures thereof. The permeable material may also include residue formed on any inanimate surface, and includes but is not limited to dust particles or grease on the inanimate surface.

As used herein, the term "inanimate surface" refers to surfaces including but not limited to fabrics, carpets, household surfaces such as floors, walls, carpet padding, towels and the like.

"Vertical orientation" as used herein, refers to a position of an air freshening product according to the present invention wherein the membrane is facing the environment in a forward facing position or in a rear facing position.

"Volatile composition" as used herein, refers to a material that is vaporizable at room temperature and atmospheric pressure without the need of an additional energy source. The composition may be configured for various uses, including but not limited to, air freshening, deodorization, odor elimination, malodor counteraction, pest control, insect control, insect repelling, medicines/medicaments, disinfectants, sanitization, mood enhancement, aromatherapy aid, scented compositions, non-scented compositions, or any other use which requires a freshening composition that acts to condition, modify, or otherwise change the atmosphere or the environment. Further, it is not necessary for all of the component materials of the composition to be volatile. Any suitable composition in any amount or form, including a liquid, solid, gel or emulsion, may be used. Materials suitable for use herein may include non-volatile compounds, such as carrier materials (e.g., water, solvents, etc.). It should also be understood that when the composition is described herein as being "delivered", "emitted", or "released", this refers to the volatization of the volatile component thereof, and does not require that the non-volatile components thereof be emitted.

"Perfume composition" as used herein includes a perfume composition comprising one or more perfume raw materials (PRMs) that is intended to treat (e.g. eliminate or reduce/minimize malodors), deliver a pleasant smell, and/or freshening the air in an interior space.

"Freshening composition" as used herein means a composition that includes a perfume composition. The freshening composition may be used with or without a device for delivering the freshening composition.

"Touch Point" as used herein, refers to a point of contact or interaction between a volatile composition and a consumer of the volatile composition.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

I. Volatile Composition

A volatile composition according to the present invention comprises a scented hydrophobic material and a RIS composition. Preferably the volatile composition is substantially free of a carrier.

The total weight ratio of the RIS composition to the scented hydrophobic material may be formulated in an effective weight ratio so as to achieve a desired scent intensity profile.

The volatile composition may be a perfume composition, preferably a freshening composition, more preferably an air freshening composition for delivering scent in an interior space. The air freshening composition may be comprised in preferably a non-energized air freshener, more preferably a continuous non-energized air freshener.

The volatile composition may comprise an effective amount of the RIS composition adapted for regulating a scent intensity. The volatile composition may comprise at least 20%, preferably 20% to 90%, more preferably 30% to 80%, of the RIS composition by weight of the volatile composition.

A technical effect of providing the RIS composition in a volatile composition is that a scent intensity of the scented hydrophobic material is reduced to improve scent experiences in the interior space, in particular at the First Touch Point at all temperatures and air flow rates.

Specifically, when the RIS composition is designed for use in a perfume composition comprising a mixture of perfume note groups (top, middle, bottom notes), each of the RIS components may be selected according to an average vapor pressure so as to slow down the evaporation rate of each respective target perfume note group by evaporating faster than the respective target perfume note group. Table 1 below shows exemplary RIS components with its respective target perfume note group and the vapor pressures.

TABLE 1

| Target Perfume Note Group | Average Vapor Pressure of a PRM in Note Group (Torr at 25° C.) | RIS component | Average Vapor Pressure of RIS component (Torr at 25° C.) |
|---|---|---|---|
| Top Note Group | 2,4-dimethylcyclohex-3-ene-1-carbaldehyde as example of a Top Note PRM (VP = 0.578 torr at 25° C.) | 3-methoxy-3-methylbutan-1-ol as example of first RIS component (VP = 0.68 torr at 25° C.) | >0.3 Torr |
| Middle Note Group | (2E)-3,7-dimethylocta-2,6-dienal as example of a Middle Note PRM (VP = 0.0712 torr at 25° C.) | dimethyl hexanedioate as example of second RIS component (VP = 0.073 torr at 25° C.) | 0.07 to 0.3 Torr |
| Bottom Note Group | 3-(3-propan-2-ylphenyl)butanal as example of a Bottom Note PRM (VP = 0.0207 torr at 25° C.) | 1-(3-methoxypropoxy)propan-1-ol as example of third RIS component (VP = 0.068 torr at 25° C.) | 0.0099 to 0.07 Torr |

The RIS composition comprising at least two of the first, second or third RIS components can measurably reduce an evaporation rate of each respective group of perfume raw materials and enables reduced vapor release rate of the perfume composition primarily by means of the RIS components evaporating faster than one or more PRMs in the corresponding group of PRMs versus being solely dependent on vapor pressures of the PRMs in the perfume composition, adding carriers to the perfume composition, or reducing an amount of the perfume composition to reduce the evaporation rate of the PRMs and to reduce a scent intensity. This enables a more consistent evaporation profile of a perfume composition in an interior space (e.g. by in head space testing by simulating the environment of an interior space in an interior environment demonstrated in results as described hereinafter under Examples) thereby producing improved scent delivery.

Specifically, the RIS composition may be configured to be low scented or non-scented relative to a perfume composition without the RIS composition. Specifically, the RIS composition may have a lower Molar Olfactive Index (MOI) relative to the perfume composition. "Molar Olfactive Index (MOI)" as used herein refers to an index that quantifies an odor intensity of a material into a value according MOI equations described hereinafter. A volatile composition having a higher MOI value correlates to a higher odor intensity relative to another composition having a lower MOI value.

Accordingly, a volatile composition having a higher MOI value corresponds to a higher scent intensity relative to another volatile composition having a lower MOI value.

A Molar Olfactive Index (MOI) of a volatile composition may be determined to identify a desired scent profile of an air freshening composition for use, for example, in continuous non-energized air fresheners, specifically evaporative air fresheners.

Specifically, the MOI of a volatile composition may be characterized by a Molar Olfactive Index (MOI) defined by Equation (I) below.

$$MOI \text{ at } y° \text{ C.} = \sum_{i,j} \frac{x_{i,j} \times P_{vap,i,j}^{sat} \text{ at } y° \text{ C.}}{ODT_{i,j}} \quad \text{Equation (I)}$$

wherein
- i=RIS component in the RIS composition;
- $x_i$=mole fraction of RIS component i;
- $p_{vap,i}^{sat}$ at y ° C.=saturation vapor pressure of RIS component i at y ° C.;
- $ODT_i$=odor detection threshold of RIS component I (ppb);
- j=component in the perfume mixture;
- $x_j$=mole fraction of component j;
- $p_{vap,j}^{sat}$ at y ° C.=saturation vapor pressure of component at y ° C.;
- $ODT_j$=odor detection threshold of component j (ppb);
- y=numerical value of the specific temperature.

The volatile composition may be characterized by a Molar Olfactive Index (MOI) Reduction Efficiency of at least 10% at 35° C. The volatile composition may be characterized by a MOI Reduction Efficiency from 10% to 100%, preferably from 25% to 65% or different combinations of the upper and lower percentages described above or combinations of any integer in the ranges listed above, at 35° C.

The MOI Reduction Efficiency of a volatile composition is determined according to Equation (II) below.

$$MOI \text{ Reduction Efficiency} = \left(1 - \frac{MOI \text{ of mixture } (RIS + \text{hydrophobic material})}{MOI \text{ of hydrophobic material}}\right) \times 100\%. \quad \text{Equation (II)}$$

Specifically, the MOI Reduction Efficiency determines a reduction in the scent intensity of a volatile composition comprising a RIS composition and a scented hydrophobic material relative to a volatile composition comprising a scented hydrophobic material but without a RIS composition. A method for determining MOI of the RIS composition is described hereinafter according to the respective components in the volatile composition.

The RIS composition may also be added in an effective amount to vary the MOI of a volatile composition. Specifically, addition of 90% of a RIS composition reduces the MOI and achieves a MOI Reduction Efficiency of 85%. The RIS composition can also be adjusted accordingly if a higher scent intensity is preferred. Therefore, use of the RIS composition provides flexibility in formulating a wide palette of scent intensities to provide a wide product range of low scented air freshening compositions and/or air freshening having a higher scent intensity based on consumer preferences.

Without wishing to be bound by theory, use of the RIS composition relative to use of traditional diluents such as 3,5,5-trimethylhexyl acetate, 3,7-dimethylocta-1,6-dien-3-ol and 4-methyl-2-(2-methylpropyl)oxan-4-ol listed in Table 2 below to reduce scent intensity is the RIS composition having the combination of at least two of the first/second/third RIS components slows down evaporation of at least two of the top/middle/bottom notes without affecting scent character.

TABLE 2

| | Vapor Pressure at 25° C. (torr) | ODT (ppb) | MOI at 35° C. | MOI less than or equal to 1 × 10⁴ at 35° C. |
|---|---|---|---|---|
| RIS composition | 3-methoxy-3-methylbutan-1-ol - 6.80 × 10⁻¹ dimethyl hexanedioate - 7.30 × 10⁻² 1-(3-methoxypropoxy)propan-1-ol - 6.80 × 10⁻² | ODT of each of the RIS components > 20 | 7.11 × 10³ | Yes |
| 3,5,5-trimethylhexyl acetate | 4.70 × 10⁻¹ | 12 (<20) | 1.09 × 10⁵ | No |
| 3,7-dimethylocta-1,6-dien-3-ol | 9.05 × 10⁻² | 22 (>20) | 1.29 × 10⁴ | No |
| 4-methyl-2-(2-methylpropyl)oxan-4-ol | 5.57 × 10⁻³ | 3 (<20) | 6.72 × 10³ | Yes |
| Combination of 3,5,5-trimethylhexyl acetate, 3,7-dimethylocta-1,6-dien-3-ol and 4-methyl-2-(2-methylpropyl)oxan-4-ol in equal mole % | | — | 4.00 × 10⁴ | No |

Referring to Table 2, the diluents, 3,5,5-trimethylhexyl acetate and 3,7-dimethylocta-1,6-dien-3-ol individually or in combination do not have a MOI of less than or equal to $1\times10^4$ at 35° C. Use of 3,5,5-trimethylhexyl acetate as a single diluent only slows an evaporation rate of the top notes but not the middle and bottom notes as it would have evaporated from the volatile composition at the start of use before the top notes, and evaporation of the middle and bottom notes would not have been controlled. Similarly use of 3,7-dimethylocta-1,6-dien-3-ol and 4-methyl-2-(2-methylpropyl)oxan-4-ol as a single diluent only addresses the middle notes and bottom notes respectively in view of the vapor pressures. A combination of 3,5,5-trimethylhexyl acetate, 3,7-dimethylocta-1,6-dien-3-ol and 4-methyl-2-(2-methylpropyl)oxan-4-ol has a MOI greater than $1\times10^4$ at 35° C. ($4.00\times10^4$) which means the scent intensity of this combination, if added to a perfume mixture having top, middle and bottom notes, may impact the scent character of the perfume mixture.

A perfume composition according to the present invention comprises a perfume mixture; and a scent intensity regulating composition (RIS composition) comprising a first scent intensity regulating component (RIS component) having an average vapor pressure (VP) greater than 0.3 Torr at 25° C.; and at least one of:

a second RIS component having an average VP from 0.07 to 0.3 Torr at 25° C.; and a third RIS component having an average VP from 0.0099 to 0.07 Torr at 25° C.;

wherein each of the first, second, and third RIS components is characterized by an Odor Detection Threshold (ODT) of greater than 20 ppb.

Figure 11:
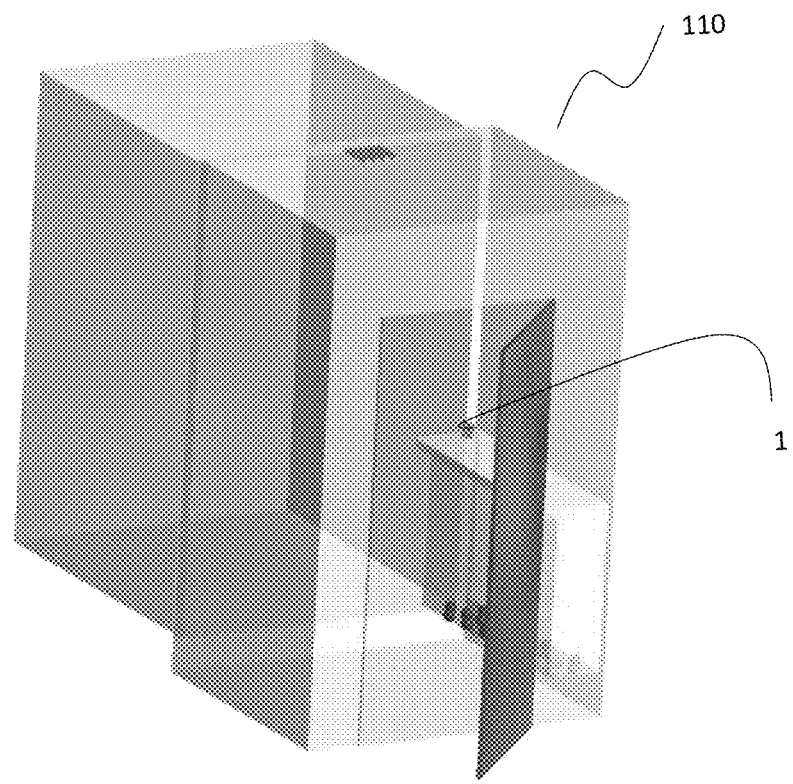
FIG. 11 is a front perspective view of an apparatus for delivering a volatile composition according to the present invention in use in an interior space of a residential environment at the entrance.

A technical effect of the combination of a first RIS component and the second RIS component or the third RIS component is that first RIS component can improve delivery of a "just nice" scent intensity by evaporating faster than the top notes which evaporate quickly to form a person's initial impression of a perfume composition without being overpowering ("too strong scent") which is very important at the First Touch Point, such as for example when an apparatus comprising the perfume composition is placed at the entrance of a residential interior space as shown in FIG. 11 described hereinafter.

Further, a scent character of a volatile composition, specifically a perfume character of a perfume composition can change at different temperatures in different seasons.

Preferably, a volatile composition of the present invention comprises a scented hydrophobic scented material wherein the scented hydrophobic material is a non-functional perfume mixture comprising one or more top notes, one or more middle notes and one or more bottom notes. At least 5% of any of the one or more top notes, the one or more middle notes, and the one or more bottom notes in the non-functional perfume mixture may comprise an odor detection threshold (ODT) less than 20, the volatile composition may be characterized by a scent character consistency variation ("SCC variation") of less than 10% within a temperature range from 5 to 35° C., wherein the SCC variation is characterized by the following Equation (III):

$$\tfrac{1}{3}\times[(\text{Max \%} - \text{Min \% of top notes}) + (\text{Max \%} - \text{Min \% of middle notes}) + (\text{Max \%} - \text{Min \% of bottom notes})] \quad \text{Equation (III)}$$

wherein

Max %=highest % within a temperature range from 5 to 35° C.;

Min %=lowest % within a temperature range from 5 to 35° C.;

wherein the one or more top notes comprises an average vapor pressure (VP) greater than 0.3 Torr at 25° C.;

wherein the one or more middle notes comprises an average VP from 0.03 to 0.3 Torr at 25° C.; and wherein the one or more bottom notes comprises an average VP less than 0.03 Torr at 25° C.

At least 25% to 65% of the one or more top notes, middle notes and bottom notes may comprise an odor detection threshold (ODT) less than 20.

This enables a more consistent scent character profile of a perfume composition in an interior space (e.g. by in head space testing by simulating the environment of an interior space in an interior environment demonstrated in results as described hereinafter under Examples) thereby producing improved scent delivery. Specifically, the Examples III to VI all demonstrate that the compositions and freshening products according to the present invention provide less scent character variation (by having SCC variation values of <10%) which enables an improved sensory impression to users.

A. RIS Composition

The RIS composition may be characterized by a Molar Olfactive Index (MOI) of less than or equal to $1\times10^4$ at 35° C., wherein MOI is defined by Equation (IV) below.

$$MOI \text{ at } 35° C. = \sum_i \frac{x_i \times P_{vap,i}^{sat} \text{ at } 35° C.}{ODT_i} \quad \text{Equation (IV)}$$

wherein i is the respective RIS component;

$x_i$=mole fraction of RIS component i;

$p_{vap,i}^{sat}$ at 35° C.=saturation vapor pressure of RIS component i at 35° C.; and $ODT_i$=ODT of RIS component i (ppb).

A highly volatile compound with a higher vapor pressure vaporizes more quickly at high temperatures relative to lower temperatures. Specifically, a RIS composition having a MOI of less than or equal to $1\times10^4$ at 35° C. means that the evaporation of the RIS composition does not or has minimum impact on the overall scent delivered in the interior space. As a result, there is improved notes suppression in a perfume composition at higher temperatures without affecting scent character, and reducing scent intensity at the same time. An inventive perfume composition according to the present invention has a reduced MOI (corresponding to a reduced scent intensity) relative to a perfume composition without a RIS composition which is demonstrated in results described hereinafter under Examples, specifically Example I. Table 3 below lists an exemplary RIS composition according to the present invention.

TABLE 3

Exemplary RIS Composition

| RIS Composition | CAS | IUPAC Name | Vapor Pressure (Torr at 25° C.) | ODT (ppb) |
|---|---|---|---|---|
| First RIS component | 56539-66-3 | 3-methoxy-3-methylbutan-1-ol (MMB) | 0.68 | 190 |
| Second RIS component | 627-93-0 | dimethyl hexanedioate (DMA) | 0.073 | 21 |
| Third RIS component | 34590-94-8 | 1-(3-methoxy-propoxy)propan-1-ol (DPM) | 0.068 | 126 |

The total weight ratio of the first RIS component to the second RIS component may be formulated in an effective weight ratio so as to achieve a MOI of less than or equal to $1 \times 10^4$ at 35° C. Further, the total weight ratio of the first RIS component, the second RIS component, and the third RIS component may be formulated in an effective weight ratio so as to achieve a MOI of less a MOI of less than or equal to $1 \times 10^4$ at 35° C.

First RIS Component

The RIS composition may comprise an effective amount of a first RIS component having an average vapor pressure (VP) greater than 0.3 Torr at 25° C. by weight of the RIS composition. Specifically, the first RIS component may be configured in an effective amount suitable for regulating a scent intensity of a volatile composition comprising a top note. Specifically, the first RIS component may be in an amount of at least 5%, from 5% to 30%, from 10% to 25%, from 15% to 25%, from 20% to 25%, or different combinations of the upper and lower percentages described above or combinations of any integer in the ranges listed above, by weight of the RIS composition. The first RIS component may be an alcohol containing compound comprising an alcohol. Specifically, the first RIS component may be a C4-C8 alcohol.

The first RIS component may be selected from the group consisting of: 3-methoxy-3-methylbutan-1-ol (MMB), 3-methylbutan-2-ol, butan-1-ol, 2,3-dimethylbutan-2-ol, 1-methoxypropan-2-ol, 2-methylbutan-2-ol, 3-methylbutan-1-ol, hex-1-en-3-ol, 2-ethylbutan-1-ol, 4-methylpentan-1-ol, 3-methylpentan-1-ol, ethyl 2-hydroxypropanoate, 2-butoxyethanol, ethyl 3-hydroxybutanoate, and mixtures thereof, more preferably selected from the group consisting of: MMB, 2-ethylbutan-1-ol, 4-methylpentan-1-ol, 3-methylpentan-1-ol, and mixtures thereof, even more preferably MMB.

The physiochemical properties of suitable compounds for a first RIS component are listed in Table 4 below.

TABLE 4

First RIS component

| IUPAC Name | GCAS | Vapor Pressure at 25° C. (torr) | ODT (ppb) |
|---|---|---|---|
| 3-methoxy-3-methylbutan-1-ol | 56539-66-3 | 6.80E−01 | 190 |
| 3-methylbutan-2-ol | 598-75-4 | 1.06E+01 | 232 |
| butan-1-ol | 71-36-3 | 8.52E+00 | 476 |
| 2,3-dimethylbutan-2-ol | 594-60-5 | 8.47E+00 | 182 |
| 1-methoxypropan-2-ol | 107-98-2 | 8.15E+00 | 1952 |

TABLE 4-continued

First RIS component

| IUPAC Name | GCAS | Vapor Pressure at 25° C. (torr) | ODT (ppb) |
|---|---|---|---|
| 2-methylbutan-2-ol | 137-32-6 | 4.76E+00 | 196 |
| 3-methylbutan-1-ol | 123-51-3 | 4.16E+00 | 240 |
| hex-1-en-3-ol | 103-05-9 | 3.60E+00 | 30 |
| 2-ethylbutan-1-ol | 97-95-0 | 1.81E+00 | 78 |
| 4-methylpentan-1-ol | 626-89-1 | 1.37E+00 | 118 |
| 3-methylpentan-1-ol | 589-35-5 | 1.26E+00 | 92 |
| ethyl 2-hydroxypropanoate | 97-64-3 | 1.16E+00 | 546 |
| 2-butoxyethanol | 111-76-2 | 5.52E−01 | 181 |
| ethyl 3-hydroxybutanoate | 5405-41-4 | 3.62E−01 | 232 |

Second RIS Component

The RIS composition may comprise an effective amount of a second RIS component having an average vapor pressure (VP) from about 0.07 to about 0.3 Torr at 25° C. by weight of the RIS composition. Specifically, the second RIS component may be configured in an effective amount suitable for regulating a scent intensity of a volatile composition comprising a middle note. Specifically, the second RIS component may be in an amount of at least 20%, from 20% to 50%, from 25% to 50%, from 30% to 45%, from 40% to 45%, or different combinations of the upper and lower percentages described above or combinations of any integer in the ranges listed above, by weight of the RIS composition. The second RIS component may be an ester containing compound. As used herein, the term "ester containing compound" refers to a compound comprising one or more acyl groups and the compound may comprise the following structure:

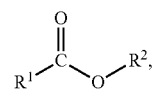

wherein:

R1 and R2 are selected from the group of substituted or unsubstituted saturated or unsaturated alkyl chains, substituted or unsubstituted cycloalkyl, and substituted or unsubstituted aryl, preferably selected from the group of substituted or unsubstituted saturated or unsaturated alkyl chains.

Specifically, the second RIS component may be a C6-C12 ester containing compound.

The second RIS component may be selected from the group consisting of: dimethyl hexanedioate (DMA), ethyl 3,5,5-trimethylhexanoate, dimethyl butanedioate, diethyl propanedioate, ethyl 3-acetyloxyhexanoate, methyl 5-acetyloxyhexanoate, 3-O-butyl 1-O-ethyl propanedioate, dipropan-2-yl hexanedioate, (4-methoxyphenyl)methyl formate, ethyl 3-hydroxyhexanoate, and mixtures thereof, more preferably selected from the group consisting of: DMA, ethyl 3-acetyloxyhexanoate, methyl 5-acetyloxyhexanoate, 3-O-butyl 1-O-ethyl propanedioate and mixtures thereof, even more preferably DMA.

The physiochemical properties of suitable compounds for a second RIS component are listed in Table 5 below.

TABLE 5

Second RIS component

| IUPAC Name | GCAS | Vapor P at 25° C. (torr) | ODT (ppb) |
|---|---|---|---|
| dimethyl hexanedioate | 627-93-0 | 7.25E−02 | 21 |
| ethyl 3,5,5-trimethylhexanoate | 67707-75-9 | 4.70E−01 | 16 |
| dimethyl butanedioate | 106-65-0 | 4.22E−01 | 56 |
| diethyl propanedioate | 105-53-3 | 3.44E−01 | 43 |
| ethyl 3-acetyloxyhexanoate | 21188-61-4 | 3.30E−01 | 29 |
| methyl 5-acetyloxyhexanoate | 35234-22-1 | 7.98E−02 | 36 |
| 3-O-butyl 1-O-ethyl propanedioate | 17373-84-1 | 5.85E−02 | 27 |
| dipropan-2-yl hexanedioate | 6938-94-9 | 1.92E−02 | 16 |
| (4-methoxyphenyl)methyl formate | 122-91-8 | 1.69E−02 | 19 |
| ethyl 3-hydroxyhexanoate | 2305-25-1 | 6.08E−03 | 48 |

Third RIS Component

The RIS composition may comprise an effective amount of a third RIS component having an average vapor pressure (VP) from about 0.0099 to about 0.07 Torr at 25° C. by weight of the RIS composition. Specifically, the third RIS component may be configured in an effective amount suitable for regulating a scent intensity of a volatile composition comprising a bottom note. The third RIS component may be in an amount of at least 10%, from 10% to 45%, from 15% to 45%, from 20% to 40%, from 30% to 40%, or different combinations of the upper and lower percentages described above or combinations of any integer in the ranges listed above, by weight of the RIS composition. The third RIS component may be an alcohol containing compound, preferably the third RIS component is a C5-C10 alcohol. The third RIS component may be selected from the group consisting of: 1-(3-methoxypropoxy)propan-1-ol (DPM), 2-(2-Methoxyethoxy)ethanol, methyl 2-hydroxybenzoate, 6,8-dimethylnonan-2-ol, 2-phenoxyethanol, 4-Oxa-1,6-hexandiol 1-(1-methyl-2-propoxyethoxy)propan-2-ol, 1-(2-butoxy-1-methoxy)propan-2-ol, and mixtures thereof, more preferably selected from the group consisting of: DPM, 2-(2-Methoxyethoxy)ethanol, 2-phenoxyethanol, 4-Oxa-1, 6-hexandiol and mixtures thereof, even more preferably DPM.

The physiochemical properties of suitable compounds for a third RIS component are listed in Table 6 below.

TABLE 6

Third RIS component

| IUPAC Name | GCAS | Vapor P at 25° C. (torr) | ODT (ppb) |
|---|---|---|---|
| 1-(3-methoxypropoxy)propan-1-ol | 34590-94-8 | 6.78E−02 | 126 |
| 2-(2-Methoxyethoxy)ethanol | 111-77-3 | 1.18E−01 | 2011 |
| methyl 2-hydroxybenzoate | 119-36-8 | 7.00E−02 | 35 |
| 6,8-dimethylnonan-2-ol | 70214-77-6 | 3.01E−02 | 68 |
| 2-phenoxyethanol | 122-99-6 | 1.55E−02 | 37 |
| 4-Oxa-1,6-hexandiol | 25265-71-8 | 9.84E−03 | 58 |
| 1-(1-methyl-2-propoxyethoxy)propan-2-ol | 29911-27-1 | 5.61E−03 | 51 |
| 1-(2-butoxy-1-methoxy)propan-2-ol | 29911-28-2 | 1.63E−03 | 39 |

B. Scented Hydrophobic Material

The volatile composition may comprise a scented hydrophobic material formulated in an effective amount such that it provides a desired scent characteristic and can be homogenously solubilized in the volatile composition to deliver a consistent scent profile.

The scented hydrophobic material may comprise a C Log P greater than 0.01, preferably from 0.01 to 6.5, more preferably from 0.5 to 5.5.

The scented hydrophobic material may be a perfume mixture comprising one or more non-functional perfume raw materials. A non-functional perfume raw material ("non-functional PRM") is utilized solely for its fragrance, scent, or hedonic benefits and does not include any of the above described first, second and third RIS components.

Equation (IV) described hereinbefore for determining the MOI of a RIS composition may be modified for use in selecting PRMs for perfume mixtures comprising fragrant top, middle, bottom notes for use, for example, in continuous non-energized air fresheners, specifically evaporative air fresheners.

Specifically, the MOI of a scented hydrophobic material such as a perfume mixture having one or more PRMs may be characterized by a Molar Olfactive Index (MOI) defined by Equation (V) below.

$$MOI \text{ at } y° C. = \sum_j \frac{x_j \times P_{vap,j}^{sat} \text{ at } y° C.}{ODT_j} \quad \text{Equation (V)}$$

wherein
j=component in perfume mixture;
$x_1$=mole fraction of component j;
$p_{vap,j}^{sat}$ at y ° C.=saturation vapor pressure of component j at y ° C.;
$ODT_j$=odor detection threshold of component j (ppb);
y=numerical value of the specific temperature.

The one or more non-functional PRMs may be selected from the group consisting of: cyclic ethylene dodecanedioate, 4-tertiary butyl cyclohexyl acetate or Vertenex™, allyl amyl glycolate, allyl caproate, allyl cyclohexane propionate, allyl heptanoate, amber xtreme, ambrox, isoamyl acetate, isoamyl propionate, anethole usp, benzyl acetate, benzyl propionate, cis-3-hexen-1-ol, beta naphthol methyl ether or nerolin, caramel furanone, caryophyllene extra, cinnamalva or Cinnamyl Nitrile, cinnamyl acetate, cinnamyl nitrile, cis-3-hexenyl butyrate, cis-3-hexenyl acetate, cis-3-hexenyl alpha methyl butyrate, cis-6-nonen-1-ol, citrathal or citral diethyl acetal, citronellol, citronellyl acetate, citronellyl butyrate, clonal or dodecane nitrile, coranol or 2,2-dimethyl cyclohexanepropanol, coumarin, cumin nitrile, cuminic alcohol, tricyclodecenyl isobutirate or cyclabute, cyclohexyl ethyl acetate, dihydromyrcenol, dimethyl anthranilate, dimethyl benzyl carbinyl acetate, dimethyl-2 6-heptan-2-ol or freesiol, sandal pentenol or ebanol, ethyl-2-methyl pentanoate, ethyl acetoacetate, ethyl linalool, ethyl maltol, ethyl phenyl glycidate, ethyl vanillin, ethyl-2-methyl butyrate, eucalyptol, eugenol, for acetate, ozone propanal or floralozone, Fructalate™ or raspberry dicarboxylate, geraniol or trans-3,7-dimethyl-2,7-octadien-1-ol, Grisalva™ or amber furan, Habanolide™ or (E)-12-musk decenone, Helvetolide™ or musk propanoate, hexyl acetate, hexyl-2-methyl butyrate, Indocolore™ or 1-phenylvinyl acetate, iso bornyl acetate, iso eugenyl acetate, iso propyl myristate, isoamyl butyrate, isoeugenol, Koumalactone™ or dihydromint lactone, laevo trisandol or sandranol, Lemonile™ or homogeranyl nitrile, Levistamel™ or mesitene lactone, linalool, linalyl acetate, linalyl iso butyrate, lymolene or dihydromyrcenol, menthol, methyl dioxolan or Fructone™, methyl iso butenyl tetrahydro pyran, methyl Pamplemousse™ or grapefruit acetal, methyl phenyl carbinyl acetate or styrallyl acetate, methyl salicylate, Montaverdi™ or green cyclopropionate, Mugetanol™ or muguet ethanol, neocaspirene, neofolione or melon nonenoate nerolidol, orange terpenes, orcinyl-3 or 3-methoxy-5-methylphenol, Oxane™ or cis-galbanum oxathiane, para cresyl methyl ether or para methyl anisole, patchouli, phenyl ethyl alcohol, phenyl ethyl dimethyl carbinol, Polysantol™ or santol pentenol, prenyl acetate, Sauvignone™ or 5-mercapto-5-methyl-3-hexanone, Sclareolate™ or clary propionate, shisolia, Strawberiff™ or 2-methyl-2-pentenoic acid, terpinolene or 4-isopropylidene-1-methylcyclohexene, tetrahydro Muguol™ or citrus ocimenol, Thesaron™ (1R,6S)-2,2,6-Trimethyl-cyclohexanecarboxylic acid ethyl ester, Tobacarol™ or 5-tetramethyl oxatricyclododecane, Undecavertol™ or violet decenol, Verdox™ or green acetate, verdural B™ or (Z)-3-hexen-1-yl isobutyrate, Violettyne™ or violet dienyne, Violiff™ or violet methyl carbonate, and mixtures thereof, preferably the one or more non-functional perfume raw materials is homogeranyl nitrile.

The one or more non-functional PRMs may be selected from the group consisting of: volatile aldehydes, ketones, and mixtures thereof.

The one or more non-functional PRMs may comprise at least one volatile aldehyde selected from the group consisting of:

Adoxal™ (2,6,10-Trimethyl-9-undecenal), Bourgeonal™ (4-t-butylbenzenepropionaldehyde), Lilestralis 33™ (2-methyl-4-t-butylphenyl)propanal), Cinnamic aldehyde, cinnamaldehyde (phenyl propenal, 3-phenyl-2-propenal), Citral, Neral (dimethyloctadienal, 3,7-dimethyl-2,6-octadien-1-al), Cyclal C™ (2,4-dimethyl-3-cyclohexen-1-carbaldehyde), Florhydral™ (3-(3-Isopropyl-phenyl)-butyraldehyde), Citronellal (3,7-dimethyl 6-octenal), Cymal (2-methyl-3-(para-isopropylphenyl)propionaldehyde), cyclamen aldehyde, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyloctan-1-al), Helional™ (3-(1,3-Benzodioxol-5-yl)-2-methylpropanal); 2-Methyl-3-(3,4-methylenedioxyphenyl)propanal), Intrel even aldehyde (undec-10-en-1-al), Ligustral™ (2,4-dimethylcyclohex-3-ene-1-carbaldehyde), Trivertal™ (2,4-dimethyl-3-cyclohexene-1-carboxaldehyde), Jasmorange™ or satinaldehyde (2-methyl-3-tolylproionaldehyde, 4-dimethylbenzenepropanal), Lyral™ (4-(4-hydroxy-4-methyl pentyl)-3-cyclohexene-1-carboxaldehyde), Melonal™ (2,6-Dimethyl-5-Heptenal), Methoxy Melonal (6-methoxy-2,6-dimethylheptanal), methoxycinnamaldehyde (trans-4-methoxycinnamaldehyde), Myrac Aldehyde™ (iso hexenyl tetraydrobenzaldehyde), Trifernal™ ((3-methyl-4-phenyl propanal, 3-phenyl butanal), lilial (3-(4-tert-Butylphenyl)-2-methylpropanal), benzenepropanal (4-tert-butyl-alpha-methyl-hydrocinnamaldehyde), Dupical™ (muguet butanal), tricyclodecylidenebutanal (4-Tricyclo5210-2,6decylidene-8butanal), Melafleur™ (1,2,3,4,5,6,7,8-octahydro-8,8-dimethyl-2-naphthaldehyde), Methyl Octyl Acetaldehyde, aldehyde C-11 MOA (2-methyl deca-1-al), Onicidal™ (2,6,10-trimethyl-5,9-undecadien-1-al), Citronellyl oxyacetaldehyde, Muguet aldehyde 50™ (3,7-dimethyl-6-octenyl) oxyacetaldehyde, phenylacetaldehyde, Mefranal™ (3-methyl-5-phenyl pentanal), dimethyl tetrahydrobenzene aldehyde (2,4-dimethyl-3-cyclohexene-1-carboxaldehyde), 2-phenyl-proprionaldehyde, Hydrotropaldehyde (2-phenyl propionaldehyde), Canthoxal™ (para-anisyl propanal), anisylpropanal 4-methoxy-alpha-methyl benzenepropanal (2-anisylidene propanal), Cyclemone A™ (1,2,3,4,5,6,7,8-octahydro-8,8-dimethyl-2-naphthaldehyde), Precyclemone B™ (1-cyclohexene-1-carboxaldehyde), mixtures thereof, preferably the one or more non-functional perfume raw materials is selected from the group consisting of: Melonal™ (2,6-Dimethyl-5-Heptenal), Methoxy Melonal (6-methoxy-2,6-dimethylheptanal), Florhydral™ (3-(3-Isopropyl-phenyl)-butyraldehyde), and mixtures thereof. The one or more non-functional perfume raw materials may comprise at least one ketone selected from the group consisting of: iso jasmone, methyl beta naphthyl ketone, musk indanone, Tonalid™ or musk tetralin, alpha-damascone, beta-damascone, delta-damascone, iso-damascone, damascenone, methyl-dihydrojasmonate, menthone, carvone, camphor, fenchone, alpha-ionone, beta-ionone, dihydro-beta-ionone, gamma-methyl ionone, alpha-methyl ionone, n-beta-methyl ionone isomer, Fleuramone™ or 2-heptylcyclopentan-1-one, dihydrojasmone, cis-jasmone, iso-e-Super™ or patchouli ethanone, methyl cedrylketone or methyl cedrylone, acetophenone, methyl-acetophenone, para-methoxy-acetophenone, methyl-beta-naphtyl-ketone, benzyl-acetone, benzophenone, para-hydroxy-phenyl-butanone, celery ketone or Livescone™, 6-isopropyl-decahydro-2-naphtone, dimethyl-octenone, Fresko-menthe™ or 2-butan-2-ylcyclohexan-1-one, 4-(1-ethoxyvinyl)-3,3,5,5,-tetramethyl-cyclohexanone, methyl-heptenone, 2-(2-(4-methyl-3-cyclohexen-1-yl) propyl)-cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4(5h)-indanone, 4-Damascol™ or pepper hexanone, Dulcinyl™ or 4-(1,3-benzodioxol-5-yl)butan-2-one, Gelsone™ or ethyl 2-acetyloctanoate, Hexalon™ or allyl alpha ionone, methyl Cyclocitrone™ or 1-(3,5,6-trimethyl-1-cyclohex-3-enyl)ethanone, methyl-lavender-Ketone™ or 3-(hydroxymethyl) nonan-2-one, Orivone™ or 4-(2-methylbutan-2-yl) cyclohexan-1-one, para-tertiary-butyl-cyclohexanone, Verdone™ or 2-tert-butylcyclohexan-1-one, Delphone™ or 2-pentylcyclopentan-1-one, muscone, Neobutenone™ or 1-(5,5-dimethyl-1-cyclohexenyl) pent-4-en-1-one, Plicatone™ or octahydro-7-methyl-1,4-methanonaphthalen-6(2H)-one, Veloutone™ or 2,2,5-trimethyl-5-pentylcyclopentan-1-one, 2,4,4,7-tetramethyl-oct-6-en-3-one, Tetrameran™ or floral undecenone, Hedione™ or methyl dihydrojasmonate, gamma undecalactone, gamma decalactone, gamma octalactone, ethylene brassylate, pentadecanolide, methyl nonyl ketone, cyclopentadecanone, 3,4,5,6-tetrahydropseudoionone, 8-hexadecenolide, dihydrojasmone, 5-cyclohexadecenone, and mixtures thereof, preferably the one or more non-functional perfume raw materials is 2-butan-2-ylcyclohexan-1-one.

C. Active Agents

The volatile composition may include an active agent. Active agents provide cleaning, surface care protection, fabric conditioning or softening, fabric refreshing, de-wrinkling, air freshening, air deodorizing, malodor removal, or like benefits in an interior space. An active agent does not include water or deionized water. In a freshening composition, the active agents may deliver a genuine malodor removal benefit. A genuine malodor removal benefit is defined as both a sensory and analytically measurable (such as by GC) malodor reduction. Thus, if the air freshening composition delivers a genuine malodor removal benefit, the air freshening composition will not function merely by using perfume to cover up or mask odors. If the air freshening product is provided with a malodor controlling agent, the air freshening product may utilize one or more of several types of odor control mechanisms. One suitable malodor controlling agent is cyclodextrin.

Active agents might also include surfactants, emulsifiers, solubilizers, polymers, malodor counteractants such as cyclodextrin, hydrogen peroxide, buffers, zinc ions, etc.

D. Optional Components

The volatile composition may, optionally, include odor masking agents, odor blocking agents. "Odor blocking" refers to the ability of a compound to dull the human sense of smell. "Odor-masking" refers to the ability of a compound to mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds.

II. Apparatus

The compositions of the present invention can be delivered to an interior space using an apparatus such as an air freshening apparatus. In the following description, the apparatus 1 described is a consumer product, such as an air freshener product, for evaporating a freshening composition in an interior occupancy space of a vehicle, an area located within a residential interior space proximal to an entrance to a residence (as shown in FIG. 11), or a bathroom containing a toilet to deliver a variety of benefits such as bacteria growth prevention, freshening, malodor removal or scenting of air in the bathroom. However, it is contemplated that the product may be configured for use in a variety of applications to deliver a freshening composition to provide the benefits in interior environments such as rooms in household and commercial establishments or furniture for storage of household items, and the air freshening product may include but is not limited to consumer products, such as, for example air freshening products, air fresheners or the like.

It is contemplated that the apparatus may be configured for a variety of applications to deliver a volatile composition to the atmosphere and/or a surface in the interior space as long as the volatile composition is evaporated from the apparatus. For the purposes of this disclosure, but without intending to limit the scope of the invention, the apparatus described is a non-energized apparatus.

The apparatus may also comprise a delivery member configured to contain a liquid phase of the composition and allow the liquid phase of the composition to evaporate therefrom. The delivery member may include a wick, a membrane, gel, porous or semi-porous substrate including a felt pad. An exemplary delivery member may be a membrane which is a semi-permeable material which allows some components of matter to pass through but stops other components. Of the components that pass through, the membrane moderates the permeation of components i.e. some components permeate faster than other components. Such components may include molecules, ions or particles.

For the purposes of illustrating the present invention in detail, the invention is described below in connection with a toilet environment and a vehicle environment. However, it will be appreciated that the invention may be implemented in any interior environment comprising a surface having a permeable material with a bacterium deposited thereon.

Figure 2:
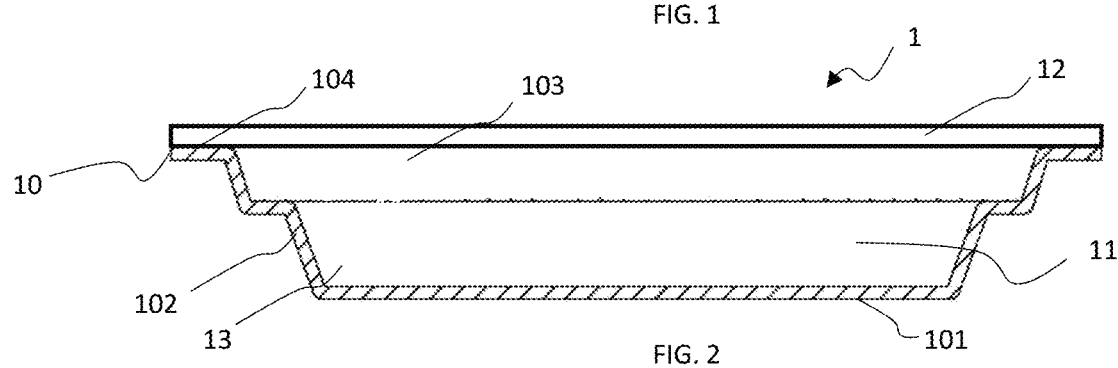
FIG. 2 is a side section view of the apparatus shown in FIG. 1 in a horizontal orientation when the apparatus is placed on a support.

FIG. 1 is a perspective view of components of a device 2 for containing a volatile composition 13 which upon assembly and filling with the composition 13, defines an apparatus 1 for delivering a volatile composition (an exemplary example is shown in FIG. 2) according to the present invention. The device 2 may be a volatile composition cartridge. Referring to FIGS. 1 and 2, the device 2 comprises a container 10 containing a reservoir 11 for containing the volatile composition 13. The container 10 may be made of a substantially vapor impermeable material designed to resist diffusion of a vapor phase of the composition 13. For example, the container 10 may be made of metal, glass, ceramic, porcelain, tile and plastic including but not limited to thermoplastics and other known materials suitable for thermoforming, injection molding and blow molding. A delivery member 12, such as for example, a membrane 12 may be disposed within the container 10 and arranged to be in fluid communication with the composition 13.

FIG. 2 shows a schematic view of the assembled apparatus 1 of FIG. 1 in a horizontal orientation with a volatile composition 13 disposed within the container 10. Referring to FIG. 2, the container 10 may comprise an end wall 101, side walls 102 and an opening 103 at a periphery 104 of the side walls 102 which define the reservoir 11. For example, if the container 12 is made of thermoplastics, the membrane 12 may be attached to the periphery 104 of the container 10 using conventional heat staking methods to contain the volatile composition 13 within the reservoir 11.

Figure 3:
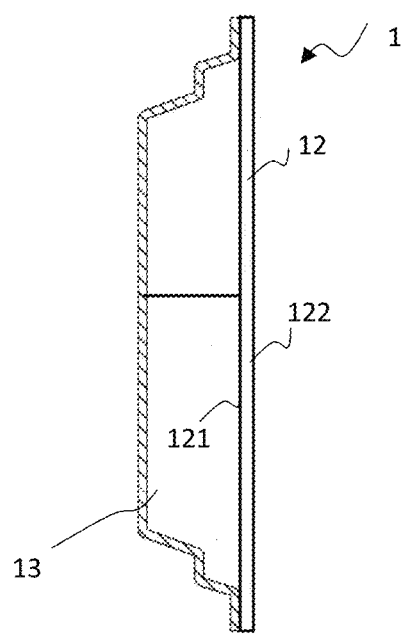
FIG. 3 is a side section view of the apparatus shown in FIG. 1 in a vertical orientation when the apparatus is placed on a support.

The apparatus 1 may be configured for use in any desired orientation, including but not limited to a vertical orientation such as shown in FIG. 3. FIG. 3 shows a side schematic view of the apparatus 1 of FIG. 1 wherein the apparatus 1 is substantially the same as the apparatus 1 of FIG. 1 except that the membrane 12 comprises a first surface 121 disposed in fluid communication with the volatile composition 13 and a second surface 122 facing the environment and away from the volatile composition 13.

Figure 4:
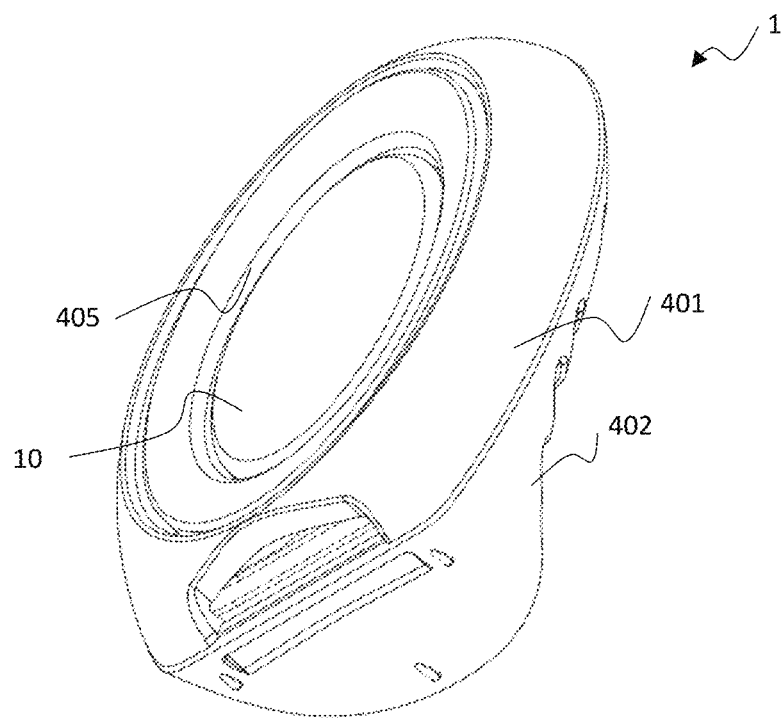
FIG. 4 is a front perspective view of a variation of an apparatus for delivering a volatile composition according to the present invention.
Figure 5:
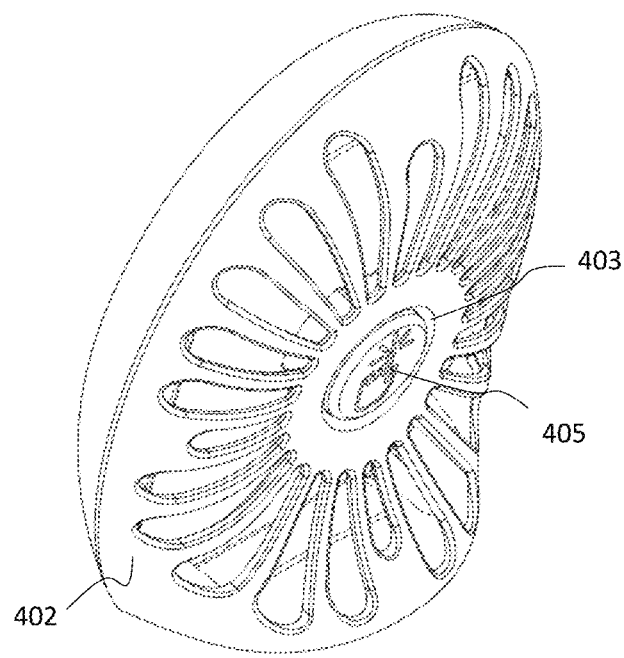
FIG. 5 is a rear perspective view of the apparatus of FIG. 4.
Figure 6:
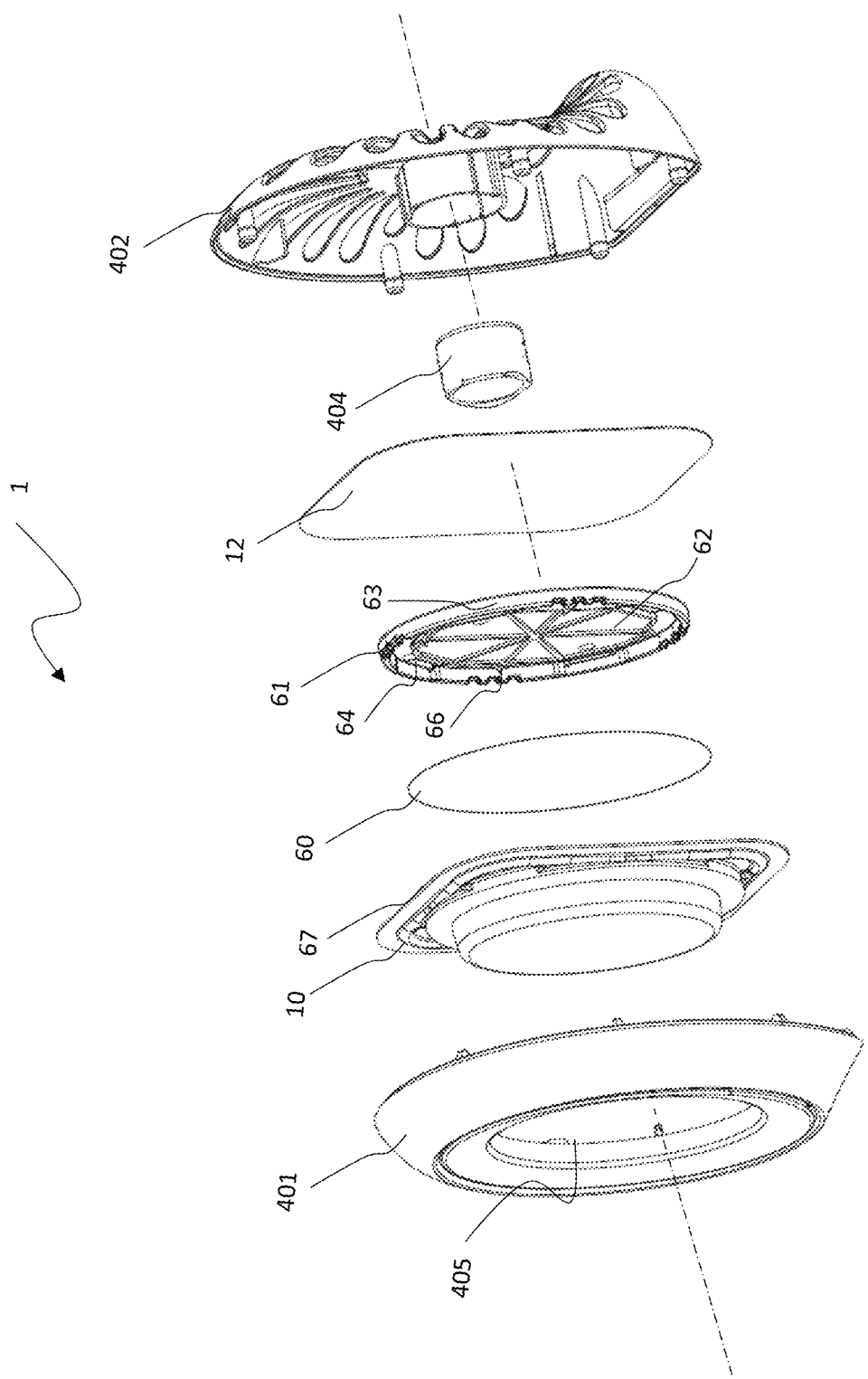
FIG. 6 is a perspective view of components of the apparatus of FIG. 4.

FIG. 4 shows a front perspective view of a further example of an apparatus 1 according to the present invention and FIG. 5 shows a rear perspective view of the apparatus 1 before use. FIG. 6 shows internal components of the apparatus 1 of FIGS. 4 and 5. The apparatus 1 of FIGS. 4, 5 and 6 comprise substantially the same features as the apparatus 1 of FIG. 1 with additional components described as follows.

Referring to FIGS. 4 and 5, the apparatus 1 comprises a housing 40 having a front cover 401 and a rear frame 402, the front cover 401 and the rear frame 402 defining an interior space. The rear frame 402 is provided with a frame opening 403 (hereinafter "opening") located substantially in the centre of the rear frame 402. An actuator 404 movable relative to the housing 40 is provided for activating the apparatus 1. The actuator 404 may be, for example, a push button 404 (hereinafter "button") disposed within the opening 403 and is movable with respect to the rear frame 402 for enabling a user to activate the apparatus 1. The container 10 containing the volatile composition 13 is located within the housing 40. The front cover 401 comprises a window 405 configured for displaying the container 10.

Referring to FIG. 6, when the volatile composition 13 is a liquid volatile composition, the apparatus 1 may comprise a rupturable substrate 60 sealably attached to and covering the reservoir 11 to prevent the volatile composition 13 from being released until the apparatus 1 is activated. The rupturable substrate 60 may be ruptured to release the volatile composition 13 by actuating a rupture mechanism 61 positioned adjacent to the rupturable substrate 60. The rupture mechanism 61 comprises a movable member 62 movably attached to an outer frame 63 by a resilient member 64. The resilient member 64 may be formed of one or more springs 65. One or more rupture elements 66 are arranged within the rupture mechanism 61 to puncture holes in the rupturable substrate 60. The rupture element 66 may be a pin. As described in the above for FIG. 1, the membrane 12 may be sealably attached to a flange 67 located at the periphery 104 of the container 10. The membrane 12 encloses the container 10, the volatile composition 13, the rupturable substrate 60, and the rupture mechanism 61. The membrane 12 may be configured to flex when a pressure or an actuation force is applied on the membrane 12 through the button 404. In a residential interior space such as a toilet having an interior space volume of 2 m$^3$, the membrane 12 may be configured to comprise an evaporative surface area from 15 cm$^2$ to 35 cm$^2$, and to achieve a compact design of the apparatus 1, the membrane 12 may comprise an evaporative surface area of 27 cm$^2$. The size and dimensions of the apparatus 1 may be configured for placement on surfaces in the interior space.

Figure 7:
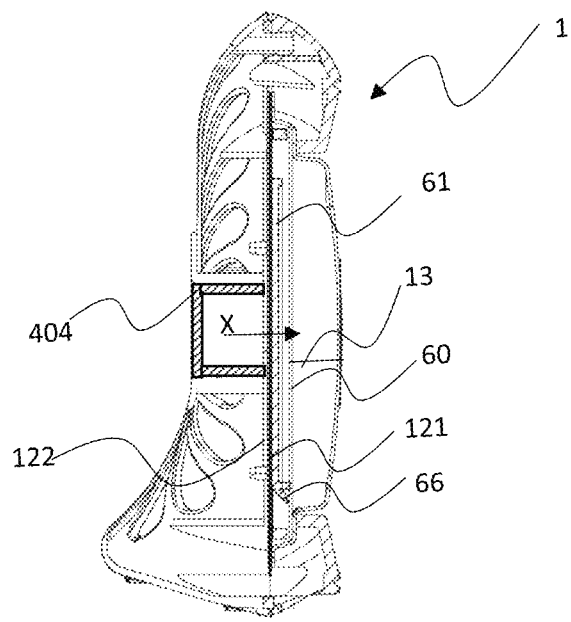
FIG. 7 is a side section view of the apparatus of FIG. 4.

Referring to FIG. 7, to activate the apparatus 1, a user depresses the button 404 until it makes contact with the rupture mechanism 61 (through the deflection of the membrane 12 in a direction X towards the front end of the container), and the rupture elements 66 on the rupture mechanism 61 pierce the rupturable substrate 60. Once the rupturable substrate 60 is pierced, the volatile composition 13 flows out of the container 10, wets the membrane 12 and is then delivered to the atmosphere surroundings through evaporation from the membrane 12. Specifically, wetting of the membrane 12 occurs when a liquid phase of the volatile composition 13 comes into contact with and spreads on at least a part of the first surface 121 of the membrane 12. The membrane 12 is configured to prevent the liquid phase of the volatile composition 13 from flowing out of the membrane 12 but enables vaporization of a vapor phase of the volatile composition 13 from the second surface 122 so that the volatile composition 13 is delivered to the environment.

The volatile composition 13 may be delivered through a wick wherein the wick may be configured to have various different shapes and sizes. For example, the wick may have a cylindrical or an elongate cube shape. The wick may be defined by a length and a diameter or width, depending on the shape. The wick may have various lengths. For example, the length of the wick may be in the range of about 1 millimeter ("mm") to about 100 mm, or from about 5 mm to about 75 mm, or from about 10 mm to about 50 mm. The wick may have various diameters or widths. For example, diameter or width of the wick may be at least 1 mm, or at least 2 mm, or at least 3 mm, or at least 4 mm. A wick may exhibit a density. The wick density may be in the range of about 0.100 grams/cm$^3$ ("g/cc") to about 1.0 g/cc. A wick may comprise a porous or semi-porous substrate. The wick may be composed of various materials and methods of construction, including, but not limited to, bundled fibers which are compressed and/or formed into various shapes via overwrap (such as a non-woven sheet over-wrap) or made of sintered plastics such as PE, HDPE or other polyolefins. For example, the wick may be made from a plastic material such as polyethylene or a polyethylene blend.

Figure 8:
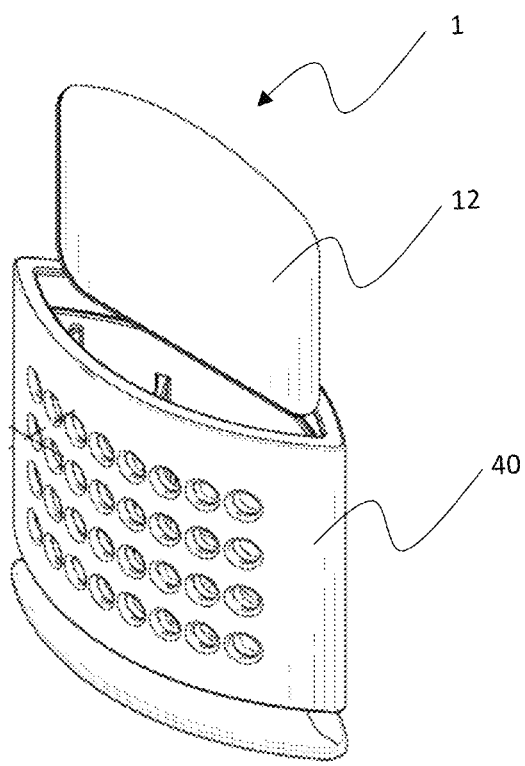
FIG. 8 is a variation of an apparatus for delivering a volatile composition according to the present invention.

FIG. 8 shows a variation of an apparatus 1 for delivering a volatile composition according to the present invention. The apparatus 1 of FIG. 8 comprise substantially the same components of the apparatus 1 of FIG. 4 except for the housing design. Specifically, the apparatus 1 of FIG. 8 does not comprise a push button and has a different housing design from the housing 40 of the apparatus 1 in that the housing 40 of FIG. 8 is configured for releasably engaging the membrane 12 enclosing the container 10 (wherein the membrane 12 and the container 10 define a delivery engine) such that the apparatus 1 is activated upon insertion of the delivery engine.

Figure 9A:
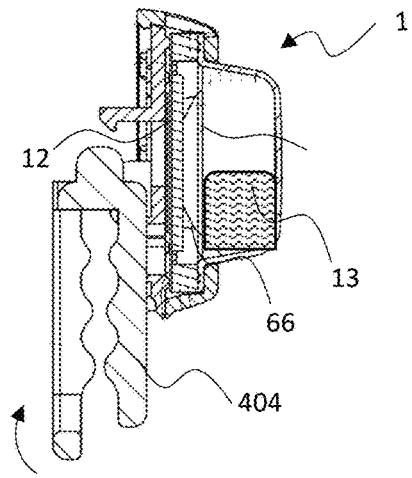
FIG. 9A is a side section view of a variation of an apparatus for delivering a volatile composition according to the present invention before activation.
Figure 9B:
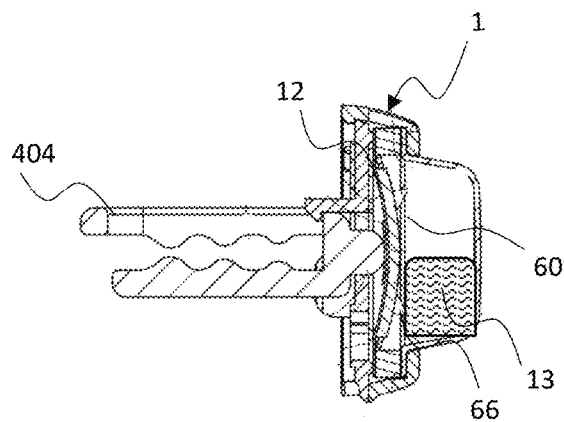
FIG. 9B is a side section view of the apparatus of FIG. 9A after activation.
Figure 9C:
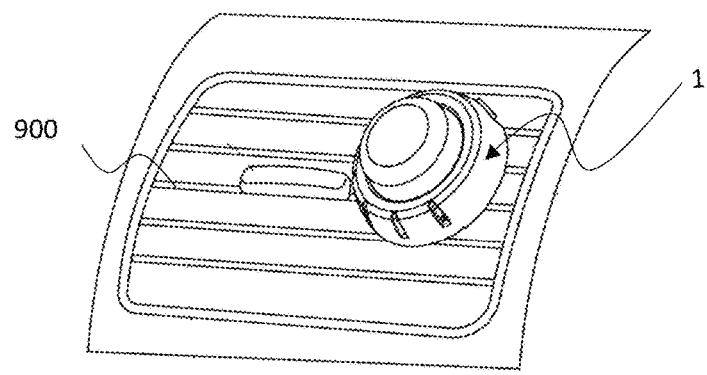
FIG. 9C is a front perspective view of the apparatus of FIGS. 9A and 9B in use in a vehicle environment.

Still further, FIGS. 9A and 9B show a variation of an apparatus 1 for delivering a volatile composition according to the present invention in a first position before activation (FIG. 9A) and a second position after activation (FIG. 9B). The apparatus 1 of FIGS. 9A and 9B differ from the apparatus 1 of FIG. 4 in that the actuator 404 is a movable clip 404 for attaching to an air vent 900 in a vehicle environment as shown in FIG. 9C. The movable clip 404 may be rotated relative to the housing 40 to move the membrane 12 and at least a portion of the rupture element 66 toward and to puncture the rupturable substrate 60 and release at least a portion of the volatile composition 13 from the container 10 such that the portion of the volatile composition 13 evaporates from the apparatus 1. It will be appreciated that the actuator 404 may be configured using known mechanical methods to move linearly or in a rotary motion so as to move the membrane 12 and at least a portion of the rupture element 66 toward and to puncture the rupturable substrate 60. In a vehicle interior space having a volume of 2 m$^3$, the membrane 12 may comprise an evaporative surface area from 7 cm$^2$ to 15 cm$^2$. To achieve a compact design of the apparatus 1, the membrane 12 may comprise an evaporative surface area of 11 cm$^2$.

FIG. 9C is a front perspective view of the apparatus 1 of FIGS. 9A and 9B in use in a vehicle environment where the apparatus 1 is located in the First Touch Point in the vehicle environment, i.e. proximate to the vehicle door that is opened for entering a vehicle interior space in the vehicle environment. The apparatus 1 may be a car air freshener product and an advantage of a car air freshener product having the volatile composition 13 with a RIS composition according to the present invention is that the user experiences a "just nice" scent intensity by evaporating faster than the top notes which evaporate quickly to form a person's initial impression of a perfume composition without being overpowering ("too strong scent") which is very important at the First Touch Point.

Figure 10:
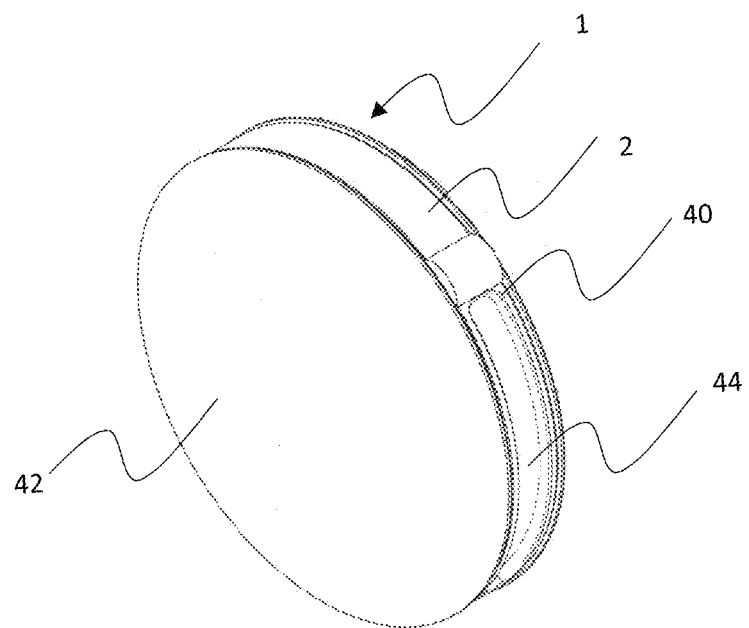
FIG. 10 is a variation of an apparatus for delivering a volatile composition according to the present invention.

FIG. 10 shows a variation of an apparatus 1 for delivering a volatile composition according to the present invention. The apparatus 1 of FIG. 10 comprises substantially the same components of the apparatus 1 of FIG. 6 except that the apparatus 1 of FIG. 10 does not comprise a push button 404, a front cover 401 and a rear frame 402. The apparatus 1 of FIG. 10 comprises a housing 40 having a disc-like shape and a housing side opening 44 at a side of the housing 40 such that the volatile composition 13 may be delivered from the side of the housing 40 through the housing side opening 44. An advantage of this configuration of an apparatus 1 in an interior environment such as in an interior space is that if there is limited table-top space, the apparatus 1 can be attached to a wall surface through a conventional vacuum suction cup so that the product 1 is proximal to the wall surface. Alternatively, the apparatus 1 may be supported in a horizontal orientation on a support in the interior environment by placing on a housing bottom surface 42 of the housing 40.

FIG. 11 is a front perspective view of an apparatus for delivering a volatile composition according to the present invention in use in an interior space 110 of a residential environment at the entrance (hereinafter "entrance interior space"). The entrance interior space 110 may comprise a volume of 2 m$^3$ and accordingly apparatus 1 described hereinbefore may be configured in any size and shape for use in the entrance interior space 110. The entrance interior space 110 is also the First Touch Point where a user first interacts with the apparatus 1 and experiences the volatile composition 13. The apparatus 1 may be designed as a room air freshener product and accordingly, an advantage of a room air freshener product having the volatile composition 13 with a RIS composition according to the present invention is that the user experiences a "just nice" scent intensity by evaporating faster than the top notes which evaporate quickly to form a person's initial impression of a perfume composition without being overpowering ("too strong scent") which is very important at the First Touch Point.

The apparatus 1 of the present invention can be configured for use in a variety of applications to deliver a volatile composition 13 to the atmosphere and/or a surface in a continuous non-energized manner as long as the composition 13 is allowed to vaporize from the membrane 12 into the interior space. Accordingly, the specific physical properties of the membrane 12 may be chosen based on the specific desired use of the apparatus 1, designed to be activated by peeling off the vapor impermeable substrate 14 or by rupturing the vapor impermeable substrate 14. Membranes and vapor impermeable substrates designed to be releasably attached are known and will not be further described. Examples of suitable physical parameters of the membrane 12 and the vapor impermeable substrate 14 suitable for an apparatus 1 designed to be activated by rupturing the vapor impermeable substrate 14 will be described hereinafter in the description.

The membrane 12 may be a microporous membrane and comprise an average pore size of about 0.01 to about 1 microns, about 0.01 to about 0.06 microns, from about 0.01 to about 0.05 microns, about 0.01 to about 0.04 microns, about 0.01 to about 0.03 microns, about 0.02 to about 0.04 microns, or about 0.02 microns. Further, the membrane 12 may be filled with any suitable filler and plasticizer known in the art. Fillers may include finely divided silica, clays, zeolites, carbonates, charcoals, and mixtures thereof. An example of a filled membrane is an ultra-high molecular weight polyethylene (UHMWPE) membrane filled with silica, such as those described in U.S. Pat. No. 7,498,369. Although any suitable fill material and weight percentage may be used, typical fill percentages for silica, may be between about 50% to about 80%, about 60% to about 80%, about 70% to about 80%, or about 70% to about 75% of the total weight of the membrane. Examples of suitable membrane thicknesses include, but are not limited to between about 0.01 mm to about 1 mm, between about 0.1 mm to 0.4 mm, about 0.15 mm to about 0.35 mm, or about 0.25 mm or different combinations of the upper and lower values described above or combinations of any integer in the ranges listed above. Still further, an evaporative surface area of the membrane 12 may be about 2 $cm^2$ to about 100 $cm^2$, about 2 $cm^2$ to about 25 $cm^2$, about 10 $cm^2$ to about 50 $cm^2$, about 10 $cm^2$ to about 45 $cm^2$, about 10 $cm^2$ to about 35 $cm^2$, about 15 $cm^2$ to about 40 $cm^2$, about 15 $cm^2$ to about 35 $cm^2$, about 20 $cm^2$ to about 35 $cm^2$, about 30 $cm^2$ to about 35 $cm^2$, about 35 $cm^2$ or different combinations of the upper and lower values described above or combinations of any integer in the ranges listed above. The membrane 12 may comprise an evaporative surface area from 2 $cm^2$ to 80 $cm^2$, from 5 $cm^2$ to 54 $cm^2$, from 6 $cm^2$ to 27 $cm^2$, from 7 $cm^2$ to 15 $cm^2$ or different combinations of the upper and lower values described above or combinations of any integer in the ranges listed above.

The vapor impermeable substrate 14 may be made of any material that can be ruptured with a pre-determined applied force, with or without the presence of an element, such as rupture element, to aid in such rupture. In embodiments where the vapor impermeable substrate 40 is intended to contain the composition 13 when the apparatus 1 is not in use, the vapor impermeable substrate 14 may be made from any suitable barrier material that reduces or prevents evaporation of the composition 13. Such materials may be impermeable to vapors and liquids. Suitable barrier materials for the vapor impermeable substrate 14 include, but are not limited to coated or uncoated films, such as polymeric films, webs, foils, and composite materials such as foil/polymeric film laminates. An example of a foil that may be used as a barrier material is a micron aluminum foil including a nitrocellulose protective lacquer, a polyurethane primer, and a 15 g/m2 polyethylene coating (Lidfoil 118-0092), available from Alcan Packaging. Suitable polymeric films include, but are not limited to, polyethylene terephtalate (PET) films, acrylonitrile copolymer barrier films such as, for example, those sold under the tradename Barex® by INOES, ethylene vinyl alcohol films, and combinations thereof. It is also contemplated that coated barrier films may be utilized as the vapor impermeable substrate 14. Such coated barrier films include, but are not limited to, metallized PET, metalized polypropylene, silica or alumina coated film.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

EXAMPLES

Test equipment/materials and test compositions are first described under Materials, then Test Methods are provided, and lastly results are discussed. Data is provided demonstrating the compositions of the present invention having improved scent intensity regulation in an interior environment. Equipment and materials used in the Test Methods described hereinafter are listed in Table 4 below. The formulations of inventive compositions are provided in Table 5 below. The compositions are prepared using conventional methods.

In the following Examples, an apparatus in which each of the test compositions and compositions of the present invention are evaluated is designed as a consumer product. The consumer product may be a car air freshener product (such as shown in FIG. 9A, 9B), for evaporating a freshening composition in a vehicle interior space to deliver a variety of benefits such as scent intensity control in the vehicle interior space. The consumer product may also be a room air freshener product (such as shown in FIG. 4), for evaporating a freshening composition in a room in a household establishment, such as a toilet. Accordingly, the equipment, materials have been designed to mimic conditions inside the vehicle interior space and the room interior space. However, it is contemplated that the apparatus may be configured for use in a variety of applications to deliver a volatile composition to provide the benefits in interior environments such as furniture for storage of personal items in household and commercial establishments, and the product may include but is not limited to consumer products, such as, for example air freshening products, air fresheners, deodorizers or the like. Therefore, in a different application whereby the interior environment has a different volume such as a shoe cabinet, it will be appreciated that the equipment, materials and methods can be modified accordingly to demonstrate the freshening compositions of the present invention having improved scent intensity regulation in an interior environment of a different volume.

Test Method(s)

A. Scent Character Consistency Variation Test Method ("SCC variation Test Method")

A scent character consistency variation ("SCC variation") of a volatile composition comprising a perfume mixture having top, middle and bottom notes as defined herein refers to a variation in a perfume character of the perfume mixture in a temperature range from 5 degrees C. to 35 degrees C. The temperature range of 5 degrees C. to 35 degrees C. can correspond to a temperature range in an interior space during different seasons namely summer, fall, winter. A test method for determining SCC variation of a volatile composition comprises the following steps:

1) Collect volatile raw materials according to the Head Space Collection Test Method described hereinafter;
2) Analyze the collected volatile raw materials according to the Head Space Analysis described hereinafter; and
3) Calculate a SCC variation of a volatile composition according to Equation (IV) described hereinbefore and reproduced below:

$$\frac{1}{3} \times [(Max\ \%-Min\ \%\ of\ top\ notes)+(Max\ \%-Min\ \%\ of\ middle\ notes)+(Max\ \%-Min\ \%\ of\ bottom\ notes)] \quad \text{Equation (IV)}$$

wherein

Max %=highest % within a temperature range from 5 to 35° C.;

Min %=lowest % within a temperature range from 5 to 35° C.;

wherein the one or more top notes comprises an average vapor pressure (VP) greater than 0.3 Torr at 25° C.;

wherein the one or more middle notes comprises an average VP from 0.03 to 0.3 Torr at 25° C.; and wherein the one or more bottom notes comprises an average VP less than 0.03 Torr at 25° C.

B. Head Space Collection Test Method

The Head Space Collection Test Method is performed to collect volatile raw materials evaporated into the interior spaces or environments defined below and according to the following steps:

1) Activate device to allow perfume to be released
2) Place device in selected enclosed environment
   a. Car simulation: Room volume is 2 m³, 3 different temperatures of 5, 21 or 35° C. with a heater, fan or air-con unit placed inside but not turned on
   b. Toilet simulation: Room volume is 2 m³, 3 different temperatures of 5, 21 or 35° C.
3) Leave device to stand for 1 hour
4) Collect head space in room using Tenex tubes at different touch points
   a. Car simulation: Collection time 2 minutes, 2 distinct touch points—upon entering room and 7 minutes after heater, cooler or fan has been turned on
   b. Toilet simulation: Collection time 1 minute, 1 touch point—upon entering room C. Head Space Analysis Through Gas Chromatography-Mass Spectroscopy (GC-MS)

The head space collected is analyzed using a GC-MS setup to identify (based on characteristic retention times and m/z values) and quantify (based on normalized peak integration areas) the disparate perfume raw materials (PRMs) that have evaporated. The PRMs are classified into either top notes, middle notes, bottom notes or bulk material. Top, middle, and bottom notes are defined as PRMs having a saturation vapor pressure at 25° C. higher than 0.3 torr, between 0.03 and 0.3 torr, and below 0.03 torr respectively. PRMs that are present with a weight percentage of more than 7% and odor detection threshold of more than 11 are classified as bulk materials, irrespective of vapor pressure.

The percentage of top notes out of all the PRMs evaporated is calculated based on the following Equation (VI):

$$\text{Percentage of top notes} = \frac{\sum \text{quantity of each top note}}{\sum \text{quantity of each } PRM} \times 100\% \quad \text{Equation (VI)}$$

Similar calculations can be made to find the percentage of middle and bottom notes.

D. Perfume Weight Loss Measurement Method

The apparatus of the present invention are characterized by the loss of the perfume mixture from the volatile composition once the apparatus is activated and for a prolonged period of time thereafter. In order to determine the efficacy of the RIS composition in improving delivery of the perfume mixture, one might look at the amount of perfume mixture released from the apparatus. Thus, it is important that this value is measured. For any volatile composition that wets a membrane, an ideal amount of evaporation of that composition occurs in a fully exposed membrane. In order to determine the efficacy of the RIS composition, one would look at the percentage weight loss of a perfume mixture in a first volatile composition (having a perfume mixture with RIS composition) and a second volatile composition (having the same perfume mixture without RIS composition). The volatile composition, however, may constitute any number of materials.

For calculation of the values detailed herein, one requires the following items:

1. Balance (Scale: Ohaus AA210 S/N 11131122540) or equivalent.
2. Housing of the present invention including a first and second wall
3. Apparatus (as shown in FIG. 4 and having a microporous membrane with an evaporative surface area of 27 cm²) containing 5.5 ml of perfume composition. Apparatus (as shown in FIG. 9A and having a microporous membrane with an evaporative surface area of 11 cm²) containing 2 ml of perfume composition. (If adding a perfume composition by weight, multiply measured density by 5.5 ml or 2 ml to obtain the accurate fill weight.)
4. 3M Scotch Weld Applicator TC and glue, #3797-TC or equivalent.
5. Evaporation rack or equivalent open tray (baker's) rack, covered at the top and shelves spaced at 15 cm or more.
6. Room to accommodate evaporating rack with the following measurements, air flow, temperature/relative humidity or equivalent:
   a) Laboratory Dimensions: 32 feet 4 inches long×72 inches wide×108 inches high or 1,730 ft³
   b) Air Flow (Intake and Exhaust)
      Normal Mode: Average Intake Supply: 103.75 ft³/min±6%
      Average Exhaust: 149.25 ft³/min±6%
      Difference results in negative air pressure: −45.5

Negative pressure indicates that air supply to laboratory and from an adjacent hallway or room is exhausted through the ventilation system.

c) Temperature and % Relative Humidity
Average Temperature: 23°+0.1° C.
Average % Relative Humidity: 45%±0.5%

Determination of Percentage of Cumulative Weight Loss of Perfume Mixture

1. Load the apparatus with the volatile composition in such a way as to provide a sealed cartridge that is not yet wetted. For instance, one may pierce a volatile composition cartridge by cutting in it a hole that allows for insertion of an 18 gauge needle.
2. Fill the apparatus of FIG. 4 with 5.5 ml of perfume composition. This is equivalent to 5024 mg of the standard perfume composition. Fill apparatus of FIG. 9A with 2 ml of perfume composition wherein 2 ml is equivalent to 1.9 grams. The volume may need to be adjusted based on the density of the composition of interest.
3. Seal the insertion hole with hot melt adhesive.
4. Measure and record the weight of the apparatus to three significant figures.
5. Insert the cartridge into the housing and ensure that the cartridge is set correctly within the housing to ensure proper air flow therethrough.
6. Activate the apparatus to wet its membrane. Herein, for an apparatus of FIG. 4, such activation is achieved by pushing the activation button of FIG. 4. For an apparatus of FIG. 9A, the apparatus is activated by moving a clip from a first position before activation (FIG. 9A) to a second position after activation (FIG. 9B) e.g. by rotating 90 degrees relative to the first position. There may, however, be equivalent means of activation and wetting the membrane.
7. Pick a time and measure (in mg) and record the cartridge weight daily at the same time for at least thirty days.
8. Determine the percentage of cumulative weight loss of the volatile composition as detailed earlier using the recorded times with their corresponding weights.

Example I—Comparative and Inventive Perfume Compositions

A perfume mixture of PRMs shown in Table 8 ("Perfume Mixture A") is combined with an exemplary RIS composition shown in Table 9 to form an Inventive Composition B for evaluation of the MOI of a volatile composition according to Equation (I) described hereinbefore. However, it will be appreciated any PRM capable of transitioning from a solid and/or liquid phase to a vapor phase may be employed.

TABLE 8

| Perfume Mixture A | | | |
|---|---|---|---|
| Ingredients by weight of the Perfume Mixture (wt %) | Mol Fraction | Vapor Pressure (Torr at 35° C.) | ODT (ppb) |
| 2,6-dimethylhept-5-enal | 0.25 | 1.26 | 8.14 |
| 2-butan-2-ylcyclohexan-1-one | 0.25 | $3.56 \times 10^{-1}$ | 2.69 |
| 3-(3-propan-2-ylphenyl)butanal | 0.25 | $5.00 \times 10^{-2}$ | 1.91 |
| 3,7-dimethylnona-2,6-dienenitrile | 0.25 | $2.25 \times 10^{-2}$ | 1.22 |

TABLE 9

| Exemplary RIS Composition | | | | | |
|---|---|---|---|---|---|
| RIS Composition | CAS | IUPAC Name | Vapor Pressure (Torr at 25° C.) | ODT (ppb) | % by weight of the RIS composition |
| First RIS component | 56539-66-3 | 3-methoxy-3-methylbutan-1-ol (MMB) | 0.68 | 190 | 22% |
| Second RIS component | 627-93-0 | dimethyl hexanedioate (DMA) | 0.073 | 21 | 42% |
| Third RIS component | 34590-94-8 | 1-(3-methoxy-propoxy)propan-1-ol (DPM) | 0.068 | 126 | 36% |

Table 10 below lists the MOI of each of the Inventive Perfume Composition B and the Comparative Perfume Composition C at 35° C.

TABLE 10

| Ingredients by weight of the composition (wt %) | Comparative Perfume Composition C | Inventive Perfume Composition B |
|---|---|---|
| Perfume Mixture A | 100% | 10% |
| RIS composition | — | 90% |
| MOI at 35° C. | $1.09 \times 10^5$ | $1.70 \times 10^4$ |

The Inventive Perfume Composition B having a MOI of $1.70 \times 10^4$ at 35° C. demonstrates that addition of a RIS composition in an amount of 90% by weight of the composition reduces a scent intensity (MOI) by approximately 85%, i.e. a MOI reduction efficiency of 85% (lower MOI value relative to the Comparative Perfume Composition A ($1.09 \times 10^5$) thereby enabling improved scent delivery in an interior space, in particular at the First Touch Point.

Example II

Example II demonstrates the way the RIS composition and the PRMs work to provide the reduced vapor release rate of the PRMs according to the present invention. It will be appreciated that the first, second and third RIS components may be formulated in any level in a RIS composition. Specifically, each of the first, second or third RIS components can be in any effective amount suitable for regulating a scent intensity of a volatile composition comprising a perfume mixture.

Figure 12:
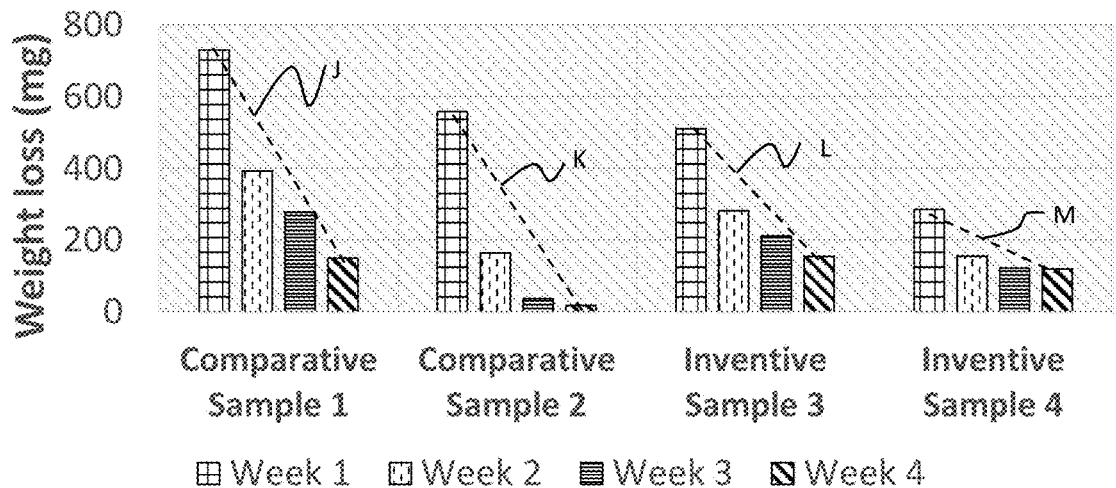
FIG. 12 is a graph plotting perfume evaporation results of Comparative Compositions (Perfume Mixture X only) and Inventive Compositions (RIS Composition and Perfume Mixture X) as a function of time.
Figure 13:
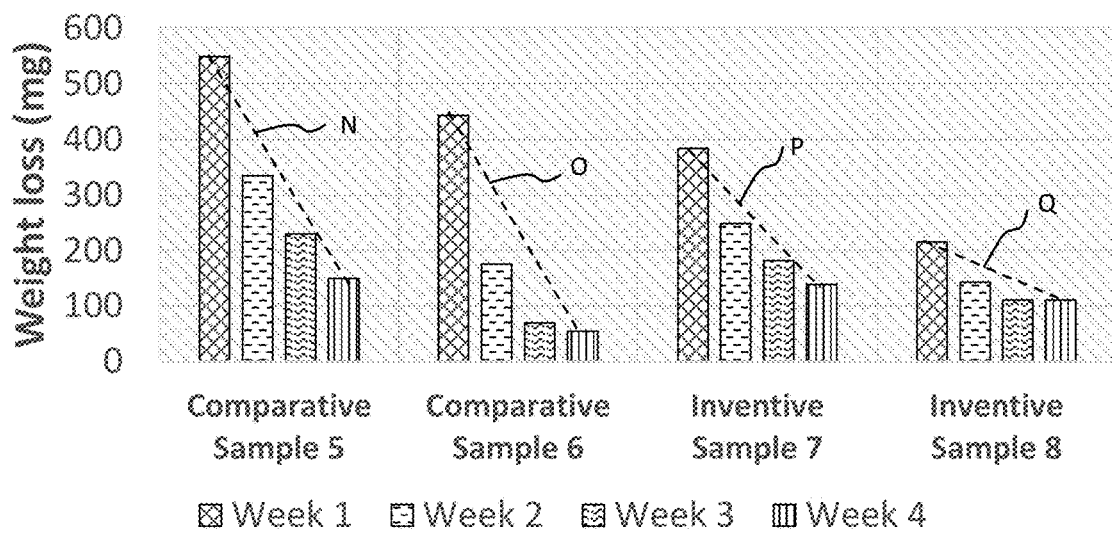
FIG. 13 is a graph plotting perfume evaporation results of Comparative Compositions (Perfume Mixture Y only) and Inventive Compositions (RIS Composition and Perfume Mixture Y) as a function of time.

Specifically, the results in Example II show that even if different perfume mixtures are used to formulate a volatile composition with a RIS composition having the same levels of first, second and third RIS components and the RIS composition is in the same level by weight of the volatile composition, the same technical result of improved scent profile is achieved based on a similar gradient in Slope L in FIG. 12 and Slope P in FIG. 13. Further, it can be seen from the different gradient of the slopes in the graphs that as evaporation is driven based on vapor pressure, inventive compositions comprising the RIS components evaporate preferentially over their respective targets—top, mid and bottom notes thus reducing a rate of evaporation and consequently reduced scent intensity at all temperatures and air flows relative to comparative compositions having perfume only.

Table 11 below lists ingredients in the Comparative Samples and Inventive Samples evaluated according to Test Method E for a period of four consecutive weeks and perfume evaporation results are tabled in Table 12 and illustrated in the graph of FIG. 12. Table 13 below lists ingredients in the Comparative Samples and Inventive Samples evaluated according to Test Method D for a period of four consecutive weeks and perfume evaporation results are tabled in Table 14 and illustrated in the graph of FIG. 13.

FIGS. 12 and 13 are graphs plotting perfume weight loss measurements of Comparative Samples and Inventive Samples against time over a period of four consecutive weeks. A line is drawn for each of the Comparative and Inventive Samples to join the peak of the perfume weight loss in the first week to the perfume weight loss in the fourth week to define a slope having a gradient, and labelled in the FIGS. 12 and 13 and in the Tables below. A slope gradient is calculated for each of slopes as shown below. A slope having a higher slope gradient value corresponds to a slope that is steeper relative to a slope having a lower slope gradient value.

TABLE 11

Comparative and Inventive Samples of FIG. 12

| By weight of the composition | Comparative Sample 1 | Comparative Sample 2 | Inventive Sample 3 | Inventive Sample 4 |
|---|---|---|---|---|
| Perfume Mixture X | 100% | 40% | 70% | 40% |
| RIS composition of Table 9 | — | — | 30% | 60% |
| Apparatus | Apparatus of FIG. 9A | Apparatus of FIG. 9A | Apparatus of FIG. 9A | Apparatus of FIG. 9A |
| Membrane evaporative surface area | 11 cm$^2$ | 11 cm$^2$ | 11 cm$^2$ | 11 cm$^2$ |

TABLE 12

Results

Perfume Mixture X: weight loss (in mg)

| Perfume evaporation | Comparative Sample 1 | Comparative Sample 2 | Inventive Sample 3 | Inventive Sample 4 |
|---|---|---|---|---|
| Week 1 | 730 | 559 | 511 | 287 |
| Week 2 | 394 | 164 | 283 | 155 |
| Week 3 | 280 | 37 | 211 | 122 |
| Week 4 | 150 | 18 | 154 | 120 |
| Slope | Slope J | Slope K | Slope L | Slope M |
| Slope Gradient | (730 − 150)/ 4 = 145 | (559 − 18)/ 4 = 135 | (511 − 154)/ 4 = 89 | (287 − 120)/ 4 = 42 |

Referring to FIG. 12, the slope J of Comparative Sample 1 has a similar steep gradient as the slope K of Comparative Sample 2 even though Comparative Sample 2 has a reduced level of Perfume Mixture X by 50%. Specifically, the slope gradient of Slope J is 145 and the slope gradient of Slope is 135. The steep gradient shows that the scent intensity is not reduced significantly for Comparative Sample 2. In contrast, the slope L of Inventive Sample 3 has a gentler gradient (slope gradient of 89) relative to the gradients of slope J and slope K indicating a reduced scent intensity across the duration of time when RIS composition is added to a volatile composition in an amount of 30% by weight of the volatile composition. Further, when the RIS composition is added in an amount of 60% by weight of the volatile composition in Inventive Sample 4, the gradient of slope M is decreased (slope gradient of 42) relative to Inventive Sample 3.

TABLE 13

Comparative and Inventive Samples of FIG. 13

| By weight of the composition | Comparative Sample 5 | Comparative Sample 6 | Inventive Sample 7 | Inventive Sample 8 |
|---|---|---|---|---|
| Perfume Mixture Y | 100% | 40% | 70% | 40% |
| RIS composition of Table 9 | — | — | 30% | 60% |
| Apparatus | Apparatus of FIG. 9A | Apparatus of FIG. 9A | Apparatus of FIG. 9A | Apparatus of FIG. 9A |
| Membrane Evaporative Surface Area | 11 cm$^2$ | 11 cm$^2$ | 11 cm$^2$ | 11 cm$^2$ |

TABLE 14

Results

Perfume mixture Y: weight loss (in mg)

| Perfume Evaporation | Comparative Sample 5 | Comparative Sample 6 | Inventive Sample 7 | Inventive Sample 8 |
|---|---|---|---|---|
| Week 1 | 549 | 443 | 384 | 216 |
| Week 2 | 335 | 176 | 249 | 142 |
| Week 2 | 230 | 69 | 182 | 110 |
| Week 3 | 150 | 54 | 138 | 110 |
| Slope | Slope N | Slope O | Slope P | Slope Q |
| Slope Gradient | (549 − 150)/ 4 = 100 | (443 − 54)/ 4 = 97 | (384 − 138)/ 4 = 62 | (216 − 110)/ 4 = 27 |

Referring to FIG. 13, the slope N and slope 0 of Comparative Samples 5 and 6 show similar gradient pattern as Comparative Samples 1 and 2, i.e. steep gradients, i.e. there is relatively little change in the slope gradients when the level of the Perfume Mixture Y is reduced in Comparative Sample 5. In contrast, the slope P and slope Q of Inventive Samples 7 and 8 respectively both have a gentle gradient indicating a reduced perfume weight loss and corresponding reduced scent intensity. Further, when the RIS composition is added in an amount of 60% by weight of the volatile composition in Inventive Sample 8, the gradient of slope Q (slope gradient of 27) is decreased relative to Inventive Sample 7 (slope gradient of 62).

Overall, the above results of the inventive compositions according to the present invention show that providing an inventive air freshening product according to the present invention in an interior environment achieves a technical effect of providing improved scent delivery by scent intensity reduction at high temperatures. Consequently, by preventing a high scent intensity at the First Touch Point, scent character may be more consistent and longevity of air freshening compositions may be improved accordingly thereby enabling dual benefits of freshening and product longevity in the interior environment. PRMs used in making the Perfume Mixtures X and Y are not disclosed by the manufacturer. However, it will be appreciated that Perfume Mixtures X and Y comprise different combinations of PRMs and as the slopes of the Comparative Samples are similar in its gradient, it can be assumed that any PRM capable of transitioning from a solid and/or liquid phase to a vapor phase may be employed.

Example III

Example III demonstrates the way the RIS composition and the PRMs work to provide a volatile composition according to the present invention with an improved scent character consistency variation ("SCC variation") of the PRMs under ambient air flow conditions in a vehicle (car) interior space, i.e. a car in a parked condition. Table 15 below lists non-functional perfume raw materials of Perfume Mixture B, used in Comparative Samples and Inventive Samples evaluated according to the SCC Test Method over a test duration from consecutive seasons of summer, autumn and winter in a year. Table 16 below lists the ingredients of each of the Comparative Samples and Inventive Samples and SCC variation results thereof are illustrated in Table 17 below.

In summary, the results of Example III show that a car air freshening composition comprising a RIS composition and non-functional perfume raw materials has an improved scent character consistency in a parked condition in any season relative to a comparative volatile composition without RIS composition by having a lower SCC variation as described hereinafter.

TABLE 15

Perfume Mixture B

| Note Type | PRM Name | wt % by weight of the Perfume Mixture |
|---|---|---|
| Top | ethyl 2-methylpentanoate | 1 |
|  | [(Z)-hex-3-enyl] acetate | 1 |
|  | 2,6-dimethylhept-5-enal | 1 |
|  | ethyl heptanoate | 2 |
|  | hexyl 2-methylpropanoate | 1 |
| Middle | decanal | 2 |
|  | 3,7-dimethylocta-1,6-dien-3-yl acetate | 12 |
|  | (2-tert-butylcyclohexyl) acetate | 9 |
|  | (1,7,7-trimethyl-2-bicyclo[2.2.1]heptanyl) acetate | 2 |
| Bottom | 2-(4-methylcyclohex-3-en-1-yl)propan-2-ol | 7 |
|  | 3-(6,6-dimethyl-2-bicyclo[3.1.1]hept-2-enyl)-2,2-dimethylpropanal | 3 |
| Bulk | 7-methyloctyl acetate | 14 |
|  | Benzyl Acetate | 14 |
|  | 3,7-dimethyloctan-3-ol | 12 |
|  | 3,7-dimethylocta-1,6-dien-3-ol | 19 |

TABLE 16

Comparative and Inventive Samples

| By weight of the composition (%) | Comparative Sample 9 | Inventive Sample 10 |
|---|---|---|
| Perfume Mixture B | 100% | 40% |
| RIS composition of Table 9 | — | 60% |
| Apparatus | FIG. 9A | FIG. 9A |
| Membrane Evaporative Surface Area | 11 cm$^2$ | 11 cm$^2$ |

TABLE 17

SCC variation results

| 1 hour Parked Condition T = 5, 21, 35° C. | Comparative Sample 9 | | | Inventive Sample 10 | | | Comparative Sample 9 Max-Min | Inventive Sample 10 Max-Min |
|---|---|---|---|---|---|---|---|---|
| Notes | Summer | Fall | Winter | Summer | Fall | Winter | (%) | (%) |
| Top | 35.0 | 62.1 | 42.8 | 23.0 | 13.7 | 26.0 | 27.1 | 12.3 |
| Middle | 3.5 | 1.4 | 16.0 | 6.0 | 0.5 | 12.4 | 14.7 | 11.9 |
| Bottom | 1.7 | 0.5 | 5.5 | 0.8 | 0.1 | 5.1 | 5.0 | 5.0 |
| SCC variation (%) | | | | | | | 15.6 (>10%) | 9.7 (<10%) |

Referring to Table 17, the Inventive Sample 10 has a SCC variation of 9.7% which is less than 10% and lower than a SCC variation of the Comparative Sample 9 (15.6%). The improvement in the SCC variation of the Invention Sample 10 is also visually demonstrated in FIG. 14A when compared with FIG. 14B described hereinafter.

Figure 14A:
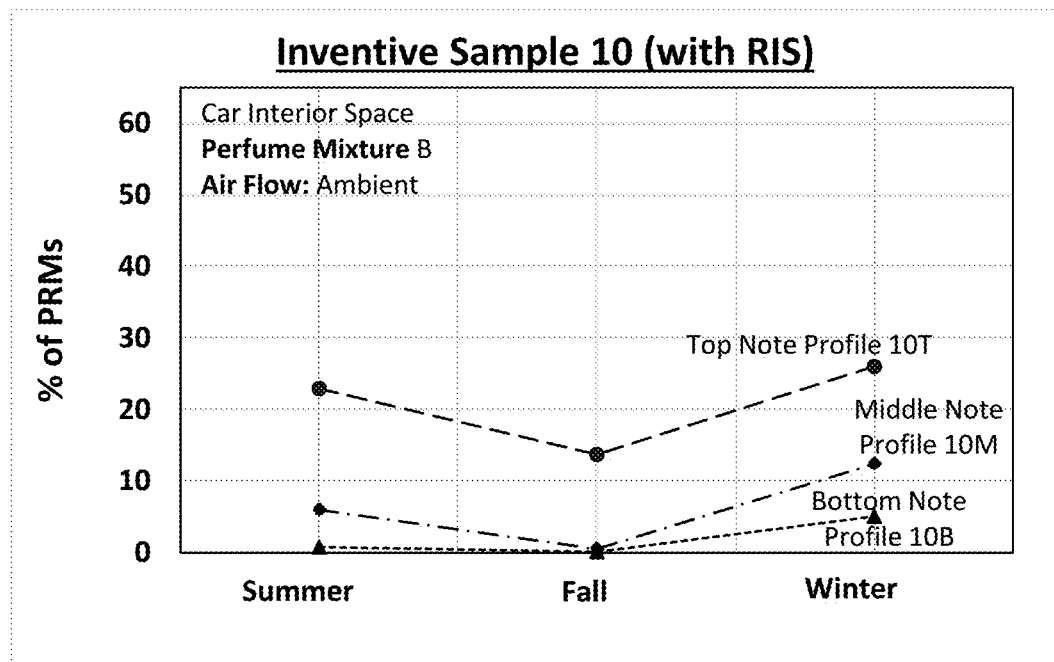
FIGS. 14A and 14B are graphs plotting a percentage of perfume raw materials (PRMs) evaporated from Inventive Sample 10 and Comparative Sample 9 in a vehicle interior space in a parked condition.
Figure 14B:
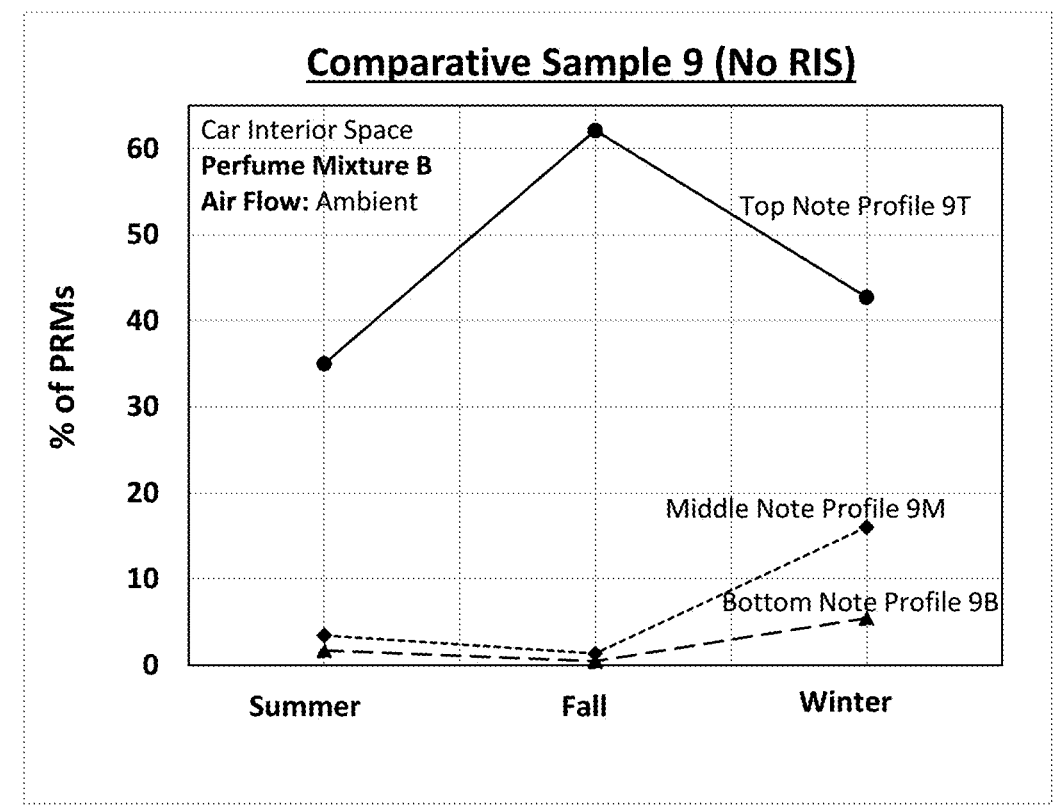

FIG. 14A is a corresponding graph of the results of Inventive Sample 10 in Table 17. FIG. 14B is a corresponding graph of the results of Comparative Sample 9 in Table 17. As shown in FIG. 14A, Inventive Sample 10 has a top note profile 10T, a middle note profile 10M and a bottom note profile 10B which are spaced closer relative to a top note profile 9T, a middle note profile 9M and a bottom note profile 9B of Comparative Sample 9.

The Inventive Sample 10 having a SCC variation of 8.6%, i.e. less than a SCC variation of 15.6% of the Comparative Sample 9 is indicative that a volatile composition having a RIS composition has an improved scent character consistency in a parked condition in any season relative to a volatile composition without a RIS composition.

Example IV

Example IV demonstrates the way the RIS composition and the PRMs work to provide a volatile composition according to the present invention with an improved scent character consistency variation ("SCC variation") of the PRMs under moving air flow conditions in a vehicle (car) interior space, i.e. a car in a driving condition. The RIS composition of Table 9 and the Perfume Mixture B of Table 15 are used to make Comparative Samples and Inventive Samples evaluated according to the SCC Test Method over a test duration from consecutive seasons of summer, autumn and winter in a year. Table 18 below lists the ingredients of each of the Comparative Samples and Inventive Samples and SCC variation results thereof are illustrated in Table 19 below.

In summary, the results of Example IV show that a car air freshening composition comprising a RIS composition and non-functional perfume raw materials has an improved scent character consistency in a driving condition in any season relative to a comparative volatile composition without RIS composition by having a lower SCC variation as described hereinafter.

TABLE 18

| Comparative and Inventive Samples | | |
|---|---|---|
| By weight of the composition (%) | Inventive Sample 11 | Comparative Sample 12 |
| Perfume Mixture B | 40% | 100% |
| RIS composition of Table 9 | 60% | — |
| Apparatus | FIG. 9A | FIG. 9A |
| Membrane Evaporative Surface Area | 11 cm$^2$ | 11 cm$^2$ |

TABLE 19

| SCC Variation Results | | | | | | | | |
|---|---|---|---|---|---|---|---|---|
| 7 minutes<br>Driving condition<br>T = 5, 21, 35° C.<br>Air flow = 4 m/s | Comparative Sample 12<br>(No RIS) | | | Inventive Sample 11<br>(with RIS) | | | Comparative Sample 12 | Inventive Sample 11 |
| Notes | Summer | Fall | Winter | Summer | Fall | Winter | Max-Min | Max-Min |
| Top | 32.6 | 45.8 | 32.1 | 27.0 | 15.7 | 16.2 | 13.8 | 11.4 |
| Middle | 4.5 | 7.4 | 14.2 | 4.0 | 1.9 | 10.3 | 9.8 | 8.3 |
| Bottom | 1.5 | 2.2 | 8.2 | 0.3 | 0.8 | 6.4 | 6.7 | 6.1 |
| SCC Variation (%) | | | | | | | 10.1% | 8.6% |

Referring to Table 18, the Inventive Sample 11 has a SCC variation of 8.6% which is less than 10% and lower than a SCC variation of the Comparative Sample 12 (10.1%). The improvement in the SCC variation of the Invention Sample 11 is also visually demonstrated in FIG. 15A when compared with FIG. 15B described hereinafter.

Figure 15A:
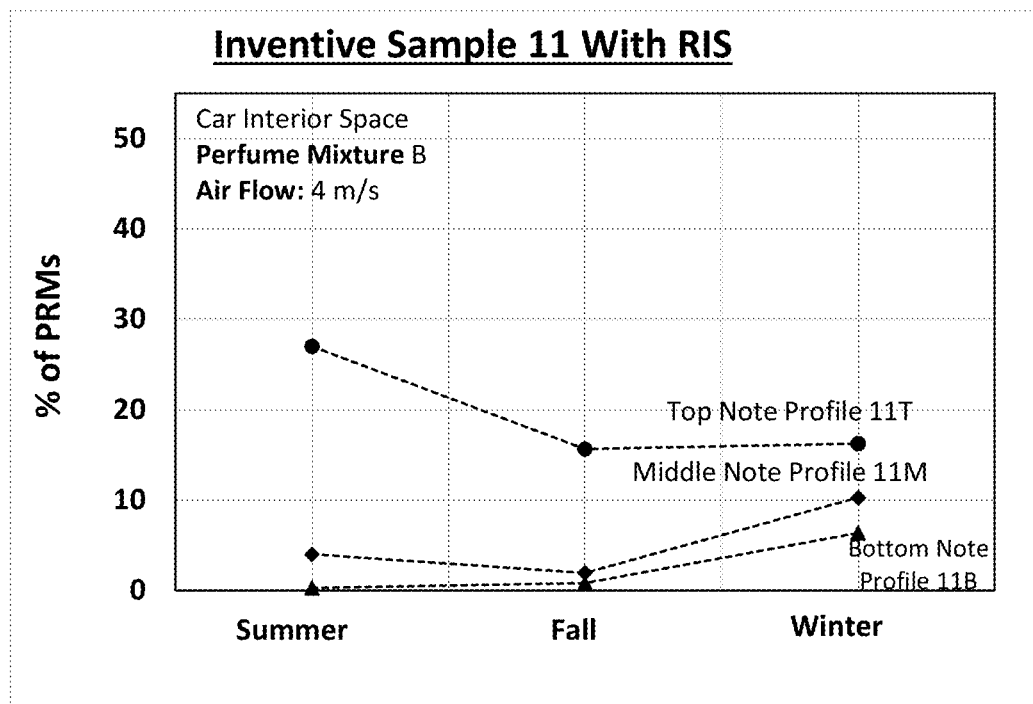
FIGS. 15A and 15B are graphs plotting a percentage of perfume raw materials (PRMs) evaporated from Inventive Sample 11 and Comparative Sample 12 in a vehicle interior space in a driving condition.
Figure 15B:
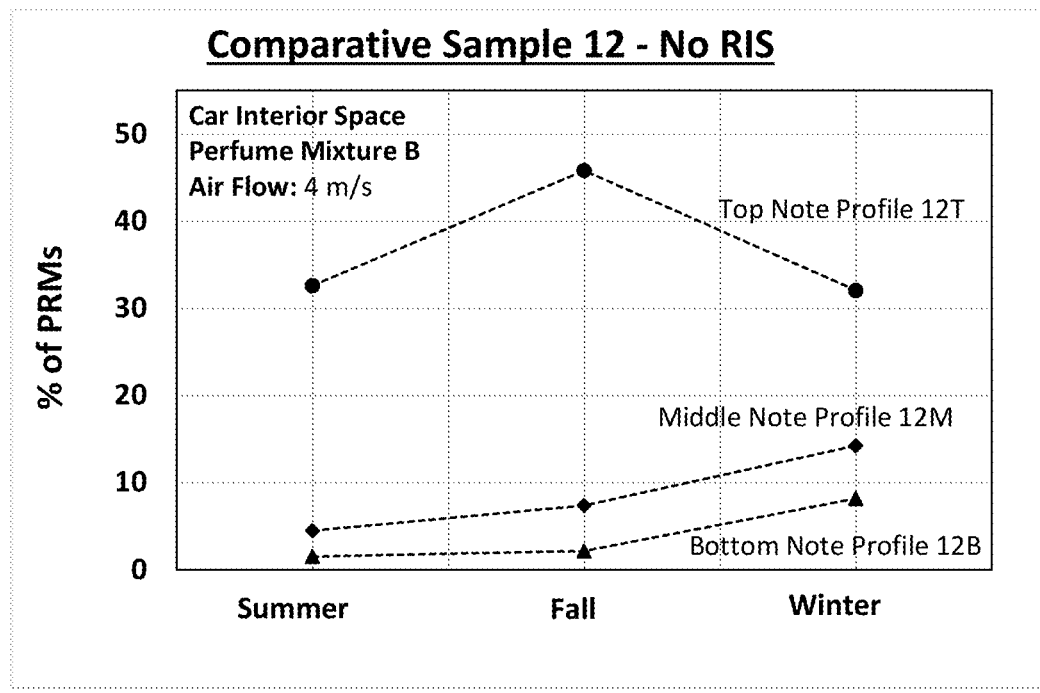

FIG. 15A is a corresponding graph of the results of Inventive Sample 11 in Table 19. FIG. 15B is a corresponding graph of the results of Comparative Sample 12 in Table 19. As shown in FIG. 15A, Inventive Sample 11 has a top note profile 11T, a middle note profile 11M and a bottom note profile 11B which are spaced closer relative to a top note profile 12T, a middle note profile 12M and a bottom note profile 12B of Comparative Sample 12.

The Inventive Sample 11 having a SCC variation of 8.6%, i.e. less than a SCC variation of 10.1% of the Comparative Sample 12 is indicative that a volatile composition having a RIS composition has an improved scent character consistency in a driving condition in any season relative to a volatile composition without a RIS composition.

Example V

Example V demonstrates the way the RIS composition and PRMs work to provide a volatile composition according to the present invention with an improved scent character consistency variation ("SCC variation") of the PRMs under moving air flow conditions in a vehicle (car) interior space, i.e. a car in a driving condition substantially the same as the driving condition in Example IV. Table 20 below lists non-functional perfume raw materials of Perfume Mixture C different from Perfume Mixture B. Perfume Mixture C is used in Comparative Samples and Inventive Samples evaluated according to the SCC Test Method over a test duration from consecutive seasons of summer, autumn and winter in a year to show that the RIS composition can be added to any PRM mixture of non-functional perfume raw materials to provide an improved scent character consistency variation. Table 21 below lists the ingredients of each of the Comparative Samples and Inventive Samples and SCC variation results thereof are illustrated in Table 22 below.

In summary, the results of Example V show that a car air freshening composition comprising a RIS composition and a different mixture of non-functional perfume raw materials also demonstrate an improved scent character consistency in a driving condition in any season relative to a comparative volatile composition without RIS composition by having a lower SCC variation as described hereinafter.

TABLE 20

Perfume Mixture C

| Note Type | IUPAC Name | wt % by weight of the Perfume Mixture C |
|---|---|---|
| Top | ethyl 2-methylbutanoate | 1 |
| | 3-methylbut-2-enyl acetate | 4 |
| | ethyl 2-methylpentanoate | 1 |
| | Hexyl Acetate | 5 |
| | 2,4-dimethylcyclohex-3-ene-1-carbaldehyde | 1 |
| | 4-methyl-2-(2-methylprop-1-enyl)oxane | 1 |
| | nonanal | 1 |
| Middle | 1-phenylethyl acetate | 5 |
| | Benzyl Acetate | 5 |
| | prop-2-enyl heptanoate | 3 |
| | (2-tert-butylcyclohexyl) acetate | 12 |
| | undec-10-enal | 1 |
| Bottom | 8-tricyclo[5.2.1.02,6]dec-3-enyl acetate | 3 |
| | (E)-1-(2,6,6-trimethylcyclohex-3-en-1-yl)but-2-en-1-one | 1 |
| | 3-(4-ethylphenyl)-2,2-dimethylpropanal | 2 |
| Bulk | ethyl 2-(2-methyl-1,3-dioxolan-2-yl)acetate | 14 |
| | 3,7-dimethyloctan-3-ol | 15 |
| | 3,7-dimethylocta-1,6-dien-3-ol | 25 |

TABLE 21

Comparative and Inventive Samples

| By weight of the composition (%) | Inventive Sample 13 | Comparative Sample 14 |
|---|---|---|
| Perfume Mixture C | 40% | 100% |
| RIS composition of Table 9 | 60% | — |
| Apparatus | FIG. 9A | FIG. 9A |
| Membrane Evaporative Surface Area | 11 cm$^2$ | 11 cm$^2$ |

TABLE 22

SCC Variation Results 7 minutes
Driving condition
T = 5, 21, 35° C.
Air flow = 4 m/s

| Notes | Comparative Sample 14 (No RIS) | | | Inventive Sample 13 (RIS) | | | Comparative Sample 14 Max-Min | Inventive Sample 13 Max-Min |
|---|---|---|---|---|---|---|---|---|
| | Summer | Fall | Winter | Summer | Fall | Winter | | |
| Top | 42.3 | 43.6 | 29.3 | 18.8 | 22.4 | 16.7 | 14.4 | 5.7 |
| Middle | 21.5 | 9.2 | 21.9 | 12.0 | 2.9 | 13.4 | 12.7 | 10.5 |
| Bottom | 0.2 | 0.2 | 6.4 | 0.1 | 0.1 | 3.3 | 6.2 | 3.2 |
| SCC Variation (%) | | | | | | | 11.1% | 6.5% |

Referring to Table 22, the Inventive Sample 13 has a SCC variation of 6.5% which is less than 10% and lower than a SCC variation of the Comparative Sample 14 (11.1%). The improvement in the SCC variation of the Invention Sample 13 is also visually demonstrated in FIG. 16A when compared with FIG. 16B described hereinafter.

Figure 16A:
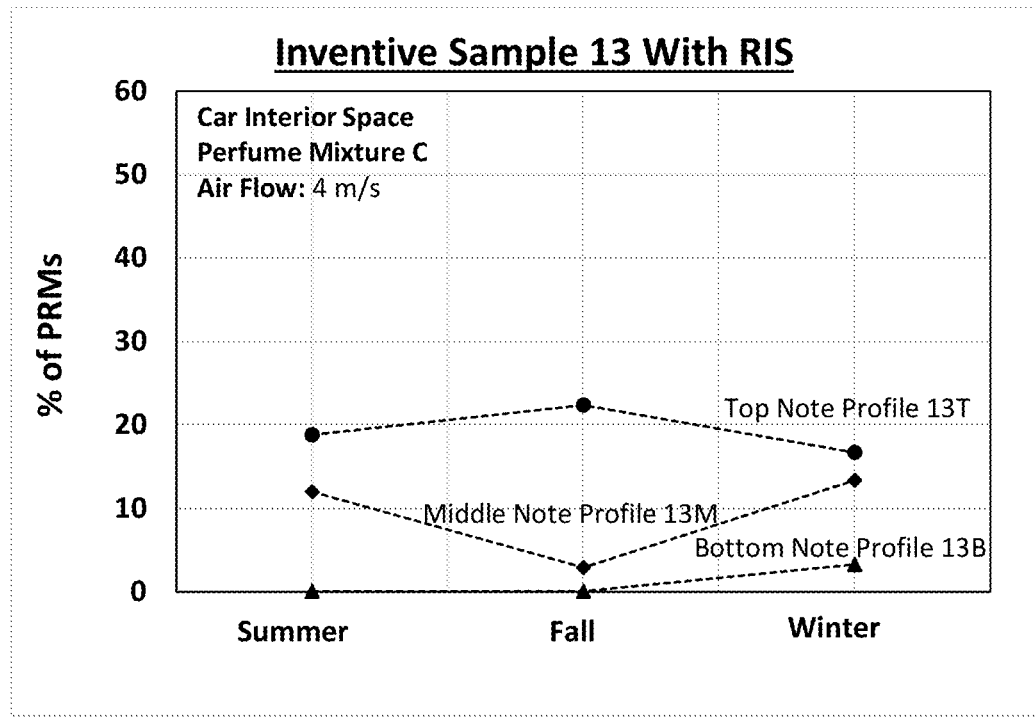
FIGS. 16A and 16B are graphs plotting a percentage of perfume raw materials (PRMs) evaporated from Inventive Sample 13 and Comparative Sample 14 in a vehicle interior space in a driving condition.
Figure 16B:
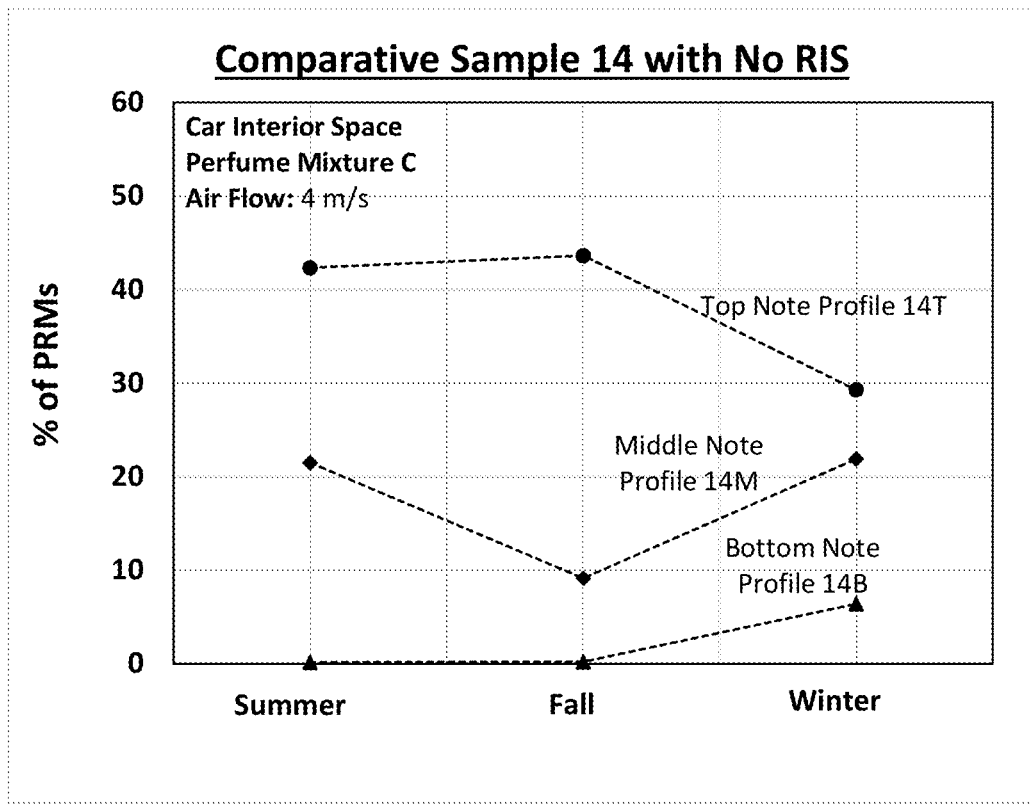

FIG. 16A is a corresponding graph of the results of Inventive Sample 13 in Table 22. FIG. 16B is a corresponding graph of the results of Comparative Sample 14 in Table 22. As shown in FIG. 16A, Inventive Sample 13 has a top note profile 13T, a middle note profile 13M and a bottom note profile 13B which are spaced closer relative to a top note profile 14T, a middle note profile 14M and a bottom note profile 14B of Comparative Sample 14.

The Inventive Sample 13 having a SCC variation of 6.5%, i.e. less than a SCC variation of 11.1% of the Comparative Sample 14 is indicative that a volatile composition having a RIS composition with any perfume mixture of non-functional perfume raw materials has an improved scent character consistency in a driving condition in any season relative to a volatile composition without a RIS composition.

Example VI

Example VI demonstrates the way the RIS composition and the PRMs work to provide a volatile composition according to the present invention with an improved scent character consistency variation ("SCC variation") of the PRMs under ambient air flow conditions in a residential (room, toilet) interior space. Table 23 below lists non-functional perfume raw materials of Perfume Mixture B, used in Comparative Samples and Inventive Samples evaluated according to the SCC Test Method over a test duration from consecutive seasons of summer, autumn and winter in a year. Table 24 below lists the ingredients of each of the Comparative Samples and Inventive Samples and SCC variation results thereof are illustrated in Table 25 below.

In summary, the results of Example VI show that a room air freshening composition comprising a RIS composition and non-functional perfume raw materials has an improved scent character consistency in ambient condition of a residential interior space having a volume of 2 m$^3$ (e.g. toilet, entrance interior space of FIG. 11) in any season relative to a comparative volatile composition without RIS composition by having a lower SCC variation as described hereinafter.

TABLE 23

Perfume Mixture D

| Note Type | IUPAC Name | wt % by weight of the Perfume Mixture |
|---|---|---|
| Top | ethyl 2-methylpentanoate | 2 |
|  | [(Z)-hex-3-enyl] acetate | 1 |
|  | (Z)-hex-3-en-1-ol | 1 |
|  | [(Z)-hex-3-enyl] methyl carbonate | 1 |
|  | 2,4-dimethylcyclohex-3-ene-1-carbaldehyde | 3 |
|  | 4-methyl-2-(2-methylprop-1-enyl)oxane | 1 |
| Middle | Decanal | 3 |
|  | 1-phenylethyl acetate | 5 |
|  | [(Z)-hex-3-enyl] butanoate | 1 |
|  | (2-tert-butylcyclohexyl) acetate | 12 |
|  | (4-tert-butylcyclohexyl) acetate | 13 |
|  | (2E,5Z)-5,6,7-trimethylocta-2,5-dien-4-one | 1 |
| Bottom | (Z)-3,4,5,6,6-pentamethylhept-3-en-2-one | 13 |
|  | 3-(4-ethylphenyl)-2,2-dimethylpropanal | 3 |
|  | (E)-1-(2,6,6-trimethylcyclohex-3-en-1-yl)but-2-en-1-one | 3 |
| Bulk | 2-methyl-6-methylideneoctan-2-ol | 10 |
|  | Benzyl Acetate | 14 |
|  | 3,7-dimethylocta-1,6-dien-3-ol | 13 |

TABLE 24

Comparative and Inventive Samples

| By weight of the composition (%) | Inventive Sample 15 | Comparative Sample 16 |
|---|---|---|
| Perfume Mixture D | 50% | 100% |
| RIS composition of Table 9 | 50% | — |
| Apparatus | FIG. 4 | FIG. 4 |
| Membrane Evaporative Surface Area | 27 cm$^2$ | 27 cm$^2$ |

TABLE 25

SCC Variation Results

| Toilet 1 hr Placement | Comparative Sample 16 (No RIS) | | | Inventive Sample 15 (RIS) | | | Comparative Sample 16 | Inventive Sample 15 |
|---|---|---|---|---|---|---|---|---|
| Notes | Summer | Fall | Winter | Summer | Fall | Winter | Max-Min | Max-Min |
| Top | 31.7 | 19.3 | 16.7 | 19.4 | 12.3 | 12.3 | 14.9 | 7.1 |
| Middle | 17.2 | 6.6 | 5.2 | 11.3 | 2.7 | 2.8 | 11.9 | 8.6 |
| Bottom | 7.6 | 3.0 | 1.8 | 5.1 | 1.3 | 1.2 | 5.8 | 3.9 |
| SCC variation (%) |  |  |  |  |  |  | 10.9% | 6.5% |

The Referring to Table 22, the Inventive Sample 15 has a SCC variation of 6.5% which is less than 10% and lower than a SCC variation of the Comparative Sample 16 (10.9%). The improvement in the SCC variation of the Invention Sample 15 is also visually demonstrated in FIG. 17A when compared with FIG. 17B described hereinafter.

Figure 17A:
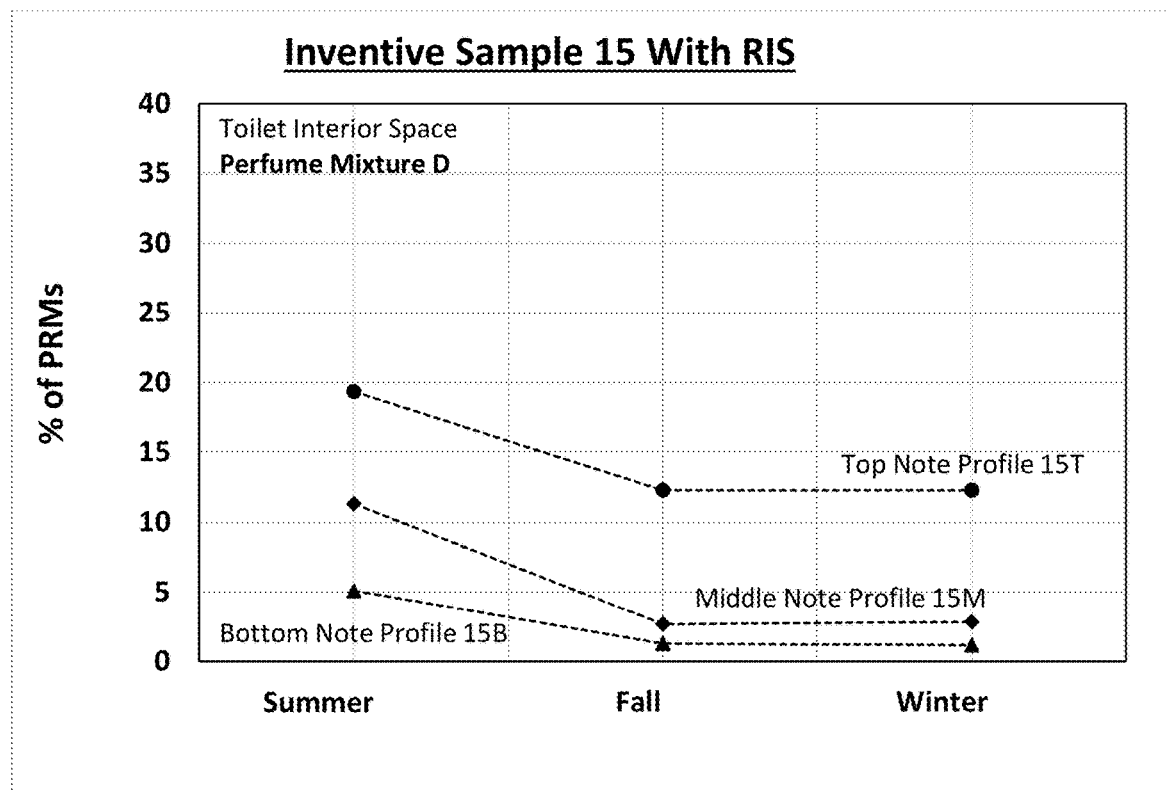
FIGS. 17A and 17B are graphs plotting a percentage of perfume raw materials (PRMs) evaporated from Inventive Sample 15 and Comparative Sample 16 in a residential interior space under ambient air flow conditions.
Figure 17B:
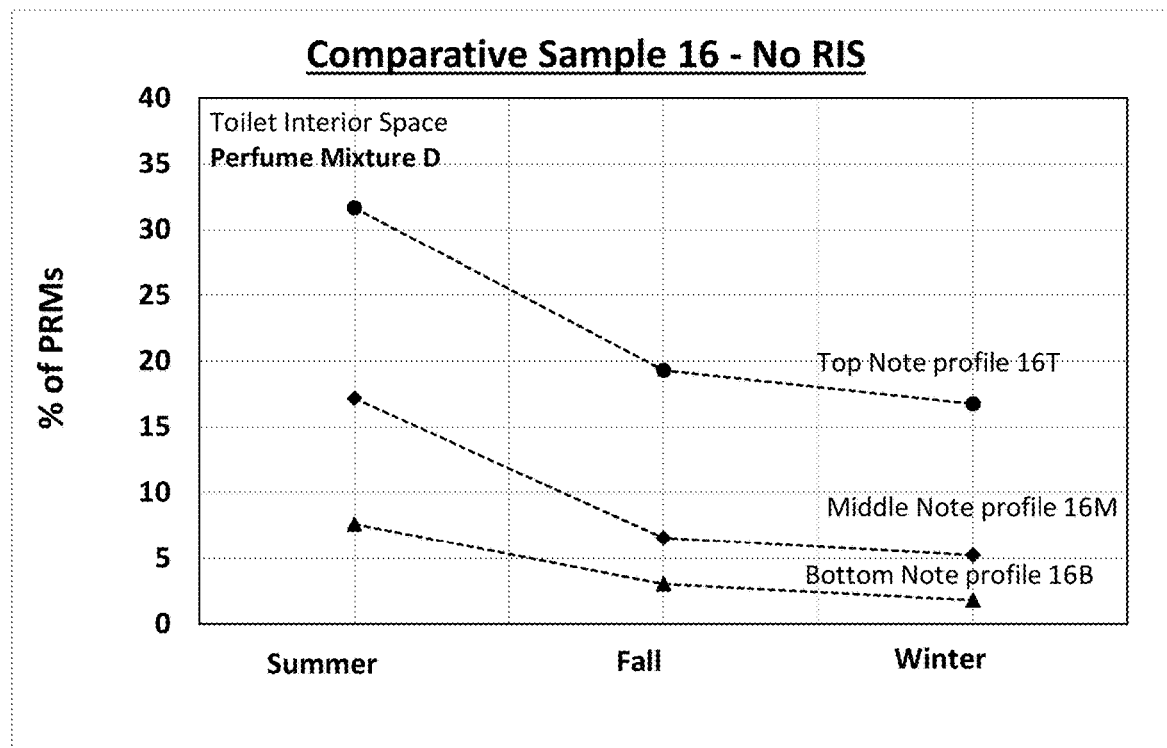

FIG. 17A is a corresponding graph of the results of Inventive Sample 15 in Table 25. FIG. 17B is a corresponding graph of the results of Comparative Sample 16 in Table 25. As shown in FIG. 17A, Inventive Sample 15 has a top note profile 15T, a middle note profile 13M and a bottom note profile 15B which are spaced closer relative to a top note profile 16T, a middle note profile 16M and a bottom note profile 16B of Comparative Sample 16.

The Inventive Sample 15 having a SCC variation of 6.5%, i.e. less than a SCC variation of 10.9% of the Comparative Sample 16 is indicative that a volatile composition having a RIS composition with any perfume mixture of non-functional perfume raw materials has an improved scent character consistency in an interior space in any season relative to a volatile composition without a RIS composition.

The above overall results show that an air freshening product having a RIS composition improves a scent character consistency (which can be impacted by temperature changes), reduces a scent intensity and has a lower SCC variation during a temperature range from 5 to 35 degrees Celsius in an interior space in different seasons. The results also demonstrate that the technical effect is achieved for any apparatus design, any membrane evaporative surface area size, any perfume mixture and under different air flow conditions (in a vehicle).

dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition comprising:
    (i) greater than 30% of a scented hydrophobic material by weight of the volatile composition, wherein the scented hydrophobic material comprises one or more volatile compounds; and
    (ii) greater than 20% of a regulating scent intensity (RIS) composition by weight of the volatile composition, wherein the RIS composition comprises at least two of:
        a first regulating scent intensity component (RIS component) having a high average vapor pressure (VP) selected from the group consisting of: 3-methoxy-3-methylbutan-1-ol (MMB), 3-methylbutan-2-ol, butan-1-ol, 2,3-dimethylbutan-2-ol, 1-methoxypropan-2-ol, 2-methylbutan-2-ol, 3-methylbutan-1-ol, hex-1-en-3-ol, 2-ethylbutan-1-ol, 4-methylpentan-1-ol, 3-methylpentan-1-ol, ethyl 2-hydroxypropanoate, 2-butoxyethanol, ethyl 3-hydroxybutanoate, and mixtures thereof;
        a second RIS component having a medium average VP is selected from the group consisting of: dimethyl hexanedioate (DMA), ethyl 3,5,5-trimethylhexanoate, dimethyl butanedioate, diethyl propanedioate, ethyl 3-acetyloxyhexanoate, 5-methyl acetyloxyhexanoate, 3-O-butyl 1-O-ethyl propanedioate, dipropan-2-yl hexanedioate, (4-methoxyphenyl) methyl formate, ethyl 3-hydroxyhexanoate, and mixtures thereof; and
        a third RIS component having a low average VP is selected from the group consisting of: 1-(3-methoxypropoxy)propan-1-ol (DPM), 2-(2-Methoxyethoxy) ethanol, methyl 2-hydroxybenzoate, 6,8-dimethylnonan-2-ol, 2-phenoxyethanol, 4-Oxa-1,6-hexandiol, 1-(1-methyl-2-propoxyethoxy)propan-2-ol, 1-(2-butoxy-1-methoxy)propan-2-ol, and mixtures thereof,
        wherein the RIS composition comprises the second RIS component;
    wherein the average VP of each of said one or more volatile compounds is lower than at least one of the high, medium and low average VPs of the first, second and third RIS components at the same temperature.

2. The volatile composition of claim 1, wherein the volatile composition is characterized by a MOI Reduction Efficiency of at least 10% at 35° C.

3. The volatile composition of claim 2, wherein the MOI Reduction Efficiency is from 25% to 65% at 35° C.

4. The volatile composition of claim 1, wherein the volatile composition comprises:
    30% to 80% of the RIS composition by weight of the volatile composition.

5. The volatile composition of claim 1, wherein the RIS composition comprises at least two of:
    at least 5% of the first RIS component by weight of the RIS composition;
    at least 20% of the second RIS component by weight of the RIS composition; and
    at least 10% of the third RIS component by weight of the RIS composition.

6. The volatile composition of claim 1, wherein the first RIS component comprises an average vapor pressure (VP) greater than 0.3 Torr at 25° C.;
    wherein the second RIS component comprises an average VP from 0.07 to 0.3 Torr at 25° C.; and wherein the third RIS component comprises an average VP from 0.0099 to 0.07 Torr at 25° C.;

wherein each of the first, second, and third RIS components is characterized by an Odor Detection Threshold (ODT) of greater than 20.

7. The volatile composition according to claim 1, wherein the first RIS component is selected from the group consisting of: MMB, 2-ethylbutan-1-ol, 4-methylpentan-1-ol, 3-methylpentan-1-ol, and mixtures thereof.

8. The volatile composition of claim 1, wherein the second RIS component is selected from the group consisting of: DMA, ethyl 3-acetyloxyhexanoate, methyl 5-acetyloxyhexanoate, 3-O-butyl 1-O-ethyl propanedioate and mixtures thereof.

9. The volatile composition of claim 1, wherein the third RIS component is selected from the group consisting of: DPM, 2-(2-Methoxyethoxy)ethanol, 2-phenoxyethanol, 4-Oxa-1,6-hexandiol and mixtures thereof.

10. The volatile composition according to claim 1, wherein the scented hydrophobic material comprises a C Log P of from 0.01 to 6.5.

11. The volatile composition of claim 1, wherein the scented hydrophobic material is a non-functional perfume mixture comprising one or more top notes, one or more middle notes, and one or more bottom notes;
wherein at least 5% of any of the one or more top notes, the one or more middle notes, and the one or more bottom notes in the non-functional perfume mixture comprise an odor detection threshold (ODT) less than 20;
wherein the volatile composition is characterized by a scent character consistency variation ("SCC variation") of less than 10% within a temperature range from 5 to 35° C.,
wherein the SCC variation is characterized by the following equation:

$$\tfrac{1}{3}\times[(\text{Max \%}-\text{Min \% of top notes})+(\text{Max \%}-\text{Min \% of middle notes})+(\text{Max \%}-\text{Min \% of bottom notes})]$$

wherein:
Max %=highest % within a temperature range from 5 to 35° C.; and
Min %=lowest % within a temperature range from 5 to 35° C.;
wherein the one or more top notes comprises an average vapor pressure (VP) greater than 0.3 Torr at 25° C.;
wherein the one or more middle notes comprises an average VP from 0.03 to 0.3 Torr at 25° C.; and
wherein the one or more bottom notes comprises an average VP less than 0.03 Torr at 25° C.

12. The volatile composition of claim 10, wherein at least 25% to 65% of the one or more top notes, the one or more middle notes, and the one or more bottom notes comprise an odor detection threshold (ODT) less than 20.

13. The volatile composition of claim 1, wherein the scented hydrophobic material is a perfume mixture comprising one or more non-functional perfume raw materials selected from the group consisting of: cyclic ethylene dodecanedioate, 4-tertiary butyl cyclohexyl acetate, allyl amyl glycolate, allyl caproate, allyl cyclohexane propionate, allyl heptanoate, amber xtreme, ambrox, isoamyl acetate, isoamyl propionate, anethole usp, benzyl acetate, benzyl propionate, cis-3-hexen-1-ol, beta naphthol methyl ether or nerolin, caramel furanone, caryophyllene extra, Cinnamyl Nitrile, cinnamyl acetate, cinnamyl nitrile, cis-3-hexenyl butyrate, cis-3-hexenyl acetate, cis-3-hexenyl alpha methyl butyrate, cis-6-nonen-1-ol, citrathal or citral diethyl acetal, citronellol, citronellyl acetate, citronellyl butyrate, clonal or dodecane nitrile, coranol or 2,2-dimethyl cyclohexanepropanol, coumarin, cumin nitrile, cuminic alcohol, tricyclodecenyl isobutirate or cyclabute, cyclohexyl ethyl acetate, dihydromyrcenol, dimethyl anthranilate, dimethyl benzyl carbinyl acetate, dimethyl-2 6-heptan-2-ol or freesiol, sandal pentenol or ebanol, ethyl-2-methyl pentanoate, ethyl acetoacetate, ethyl linalool, ethyl maltol, ethyl phenyl glycidate, ethyl vanillin, ethyl-2-methyl butyrate, eucalyptol, eugenol, flor acetate, ozone propanal or floralozone, raspberry dicarboxylate, geraniol or trans-3,7-dimethyl-2,7-octadien-1-ol, amber furan, (E)-12-musk decenone, or musk propanoate, hexyl acetate, hexyl-2-methyl butyrate, 1-phenylvinyl acetate, iso bornyl acetate, iso eugenyl acetate, iso propyl myristate, isoamyl butyrate, isoeugenol, dihydromint lactone, laevo trisandol or sandranol, homogeranyl nitrile, mesitene lactone, linalool, linalyl acetate, linalyl iso butyrate, lymolene or dihydromyrcenol, menthol, methyl dioxolan, methyl iso butenyl tetrahydro pyran, or grapefruit acetal, methyl phenyl carbinyl acetate or styrallyl acetate, methyl salicylate, green cyclopropionate, muguet ethanol, neocaspirene, neofolione or melon nonenoate nerolidol, orange terpenes, orcinyl-3 or 3-methoxy-5-methylphenol, cis-galbanum oxathiane, para cresyl methyl ether or para methyl anisole, patchouli, phenyl ethyl alcohol, phenyl ethyl dimethyl carbinol, santol pentenol, prenyl acetate, 5-mercapto-5-methyl-3-hexanone, clary propionate, shisolia, 2-methyl-2-pentenoic acid, terpinolene or 4-isopropylidene-1-methylcyclohexene, citrus ocimenol, 1R,6S)-2,2,6-Trimethyl-cyclohexanecarboxylic acid ethyl ester, 5-tetramethyl oxatricyclododecane, violet decenol, green acetate, (Z)-3-hexen-1-yl isobutyrate, violet dienyne, violet methyl carbonate, and mixtures thereof.

14. The volatile composition of claim 1, wherein the scented hydrophobic material is a perfume mixture comprising one or more non-functional perfume raw materials selected from the group consisting of: volatile aldehydes, ketones, and mixtures thereof.

15. The volatile composition of claim 14, wherein the one or more non-functional perfume raw materials comprises at least one volatile aldehyde selected from the group consisting of:
2,6,10-Trimethyl-9-undecenal, 4-t-butylbenzenepropionaldehyde, 2-methyl-4-t-butylphenyl)propanal, Cinnamic aldehyde, cinnamaldehyde (phenyl propenal, 3-phenyl-2-propenal), Citral, Neral (dimethyloctadienal, 3,7-dimethyl-2,6-octadien-1-al), 2,4-dimethyl-3-cyclohexen-1-carbaldehyde, 3-(3-Isopropyl-phenyl)-butyraldehyde, Citronellal (3,7-dimethyl 6-octenal), Cymal (2-methyl-3-(para-isopropylphenyl) propionaldehyde), cyclamen aldehyde, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), 3-(1,3-Benzodioxol-5-yl)-2-methylpropanal; 2-Methyl-3-(3,4-methylenedioxyphenyl)propanal), Intreleven aldehyde (undec-10-en-1-al), 2,4-dimethylcyclohex-3-ene-1-carbaldehyde, 2,4-dimethyl-3-cyclohexene-1-carboxaldehyde, satinaldehyde (2-methyl-3-tolylproionaldehyde, 4-dimethylbenzenepropanal), 4-(4-hydroxy-4-methyl pentyl)-3-cyclohexene-1-carboxaldehyde, 2,6-Dimethyl-5-Heptenal, Methoxy Melonal (6-methoxy-2,6-dimethylheptanal), methoxycinnamaldehyde (trans-4-methoxycinnamaldehyde), Myrac aldehyde iso hexenyl tetraydrobenzaldehyde), (3-methyl-4-phenyl propanal, 3-phenyl butanal, lilial (3-(4-tert-Butylphenyl)-2-methylpropanal), benzenepropanal (4-tert-butyl-alpha-methyl-hydrocinnamaldehyde), muguet butanal, tricyclodecylidenebutanal (4-Tricyclo5210-2,6decylidene-8butanal), 1,2,3,4,5,6,7,8-octahydro-8,8-dimethyl-2-naphthaldehyde, Methyl Octyl Acetaldehyde, aldehyde C-11 MOA (2-methyl deca-1-al), 2,6,10-trimethyl-5,9-undecadien-1-al, Citronellyl oxyacetaldehyde, Muguet aldehyde 50 3,7- dimethyl-6-octenyl) oxyacetaldehyde, phenylacetaldehyde, 3-methyl-5-phenyl pentanal, dimethyl tetrahydrobenzene aldehyde (2,4-dimethyl-3-cyclohexene-1-carboxaldehyde), 2-phenylproprionaldehyde, Hydrotropaldehyde (2-phenyl propionaldehyde), para-anisyl propanal, anisylpropanal 4-methoxy-alpha-methyl benzenepropanal (2-anisylidene propanal), 1,2,3,4,5,6,7,8-octahydro-8,8-dimethyl-2-naphthaldehyde, 1-cyclohexene-1-carboxaldehyde, mixtures thereof.

16. The volatile composition according to claim 14, wherein the one or more non-functional perfume raw materials comprises at least one ketone selected from the group consisting of:

iso jasmone, methyl beta naphthyl ketone, musk indanone, musk tetralin, alpha-damascone, beta-damascone, delta-damascone, iso-damascone, damascenone, methyl-dihydrojasmonate, menthone, carvone, camphor, fenchone, alpha-ionone, beta-ionone, dihydro-beta-ionone, gamma-methyl ionone, alpha-methyl ionone, n-beta-methyl ionone isomer, 2-heptylcyclopentan-1-one, dihydrojasmone, cis-jasmone, patchouli ethanone, methyl cedrylketone or methyl cedrylone, acetophenone, methyl-acetophenone, para-methoxy-acetophenone, methyl-beta-naphtyl-ketone, benzyl-acetone, benzophenone, para-hydroxy-phenyl-butanone, celery ketone, 6-isopropyldecahydro-2-naphtone, dimethyl-octenone, 2-butan-2-ylcyclohexan-1-one, 4-(1-ethoxyvinyl)-3,3,5,5,-tetramethyl-cyclohexanone, methyl-heptenone, 2-(2-(4-methyl-3-cyclohexen-1-yl)propyl)-cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4(5h)-indanone, pepper hexanone, 4-(1,3-benzodioxol-5-yl) butan-2-one, ethyl 2-acetyloctanoate, allyl alpha ionone, 1-(3,5,6-trimethyl-1-cyclohex-3-enyl)ethanone, 3-(hydroxymethyl)nonan-2-one, 4-(2-methylbutan-2-yl)cyclohexan-1-one, para-tertiary-butyl-cyclohexanone, 2-tert-butylcyclohexan-1-one, 2-pentylcyclopentan-1-one, muscone, 1-(5,5-dimethyl-1-cyclohexenyl)pent-4-en-1-one, or octahydro-7-methyl-1,4-methanonaphthalen-6(2H)-one, 2,2,5-trimethyl-5-pentylcyclopentan-1-one, 2,4,4,7-tetramethyl-oct-6-en-3-one, floral undecenone, or methyl dihydrojasmonate, gamma undecalactone, gamma decalactone, gamma octalactone, ethylene brassylate, pentadecanolide, methyl nonyl ketone, cyclopentadecanone, 3,4,5,6-tetrahydropseudoionone, 8-hexadecenolide, dihydrojasmone, 5-cyclohexadecenone, and mixtures thereof.

17. The volatile composition of claim 1, wherein the volatile composition is an air freshening composition for delivering scent in an interior space; wherein the air freshening composition is comprised in a continuous non-energized air freshener.

18. An apparatus for delivering a volatile composition in an interior space, the apparatus comprising:
a reservoir for containing a volatile composition according to claim 1, the reservoir including an opening; wherein the volatile composition comprises a liquid phase; and
a delivery member configured to contain and allow the liquid phase of the volatile composition to evaporate therefrom; wherein the interior space is one of: a vehicle interior space, an interior space of a residential environment, a toilet, an interior space of commercial environment.

19. The apparatus of claim 18, wherein the delivery member is selected from the group consisting of: a wick, a microporous membrane, a gel, a porous or semi-porous substrate.

20. An air freshening product comprising a volatile composition having:
(i) a non-functional perfume mixture comprising one or more top notes, one or more middle notes and one or more bottom notes; wherein at least 5% of any of the one or more top notes, the one or more middle notes, and the one or more bottom notes in the non-functional perfume mixture comprise an odor detection threshold (ODT) less than 20; and
(ii) a regulating scent intensity (RIS) composition by weight of the volatile composition, wherein the RIS composition comprises at least two of:
a first regulating scent intensity component (RIS component) having a high average vapor pressure (VP);
a second RIS component having a medium average VP; and
a third RIS component having a low average VP;
wherein the average VP of each of one or more top notes, one or more middle notes, one or more bottom notes is lower than a corresponding one of the high, medium and low average VPs of the first, second and third RIS components at the same temperature;
wherein the volatile composition is characterized by a scent character consistency variation ("SCC variation") of less than 10% within a temperature range from 5 to 35° C., wherein the SCC variation is characterized by the following equation:

$$\tfrac{1}{3}\times[(\text{Max \%}-\text{Min \% of top notes})+(\text{Max \%}-\text{Min \% of middle notes})+(\text{Max \%}-\text{Min \% of bottom notes})]$$

wherein
Max %=highest % within a temperature range from 5 to 35° C.;
Min %=lowest % within a temperature range from 5 to 35° C.;
wherein the one or more top notes comprises an average vapor pressure (VP) greater than 0.3 Torr at 25° C.;
wherein the one or more middle notes comprises an average VP from 0.03 to 0.3 Torr at 25° C.; and
wherein the one or more bottom notes comprises an average VP less than 0.03 Torr at 25° C.

* * * * *